United States Patent

Breu et al.

[11] Patent Number: 5,837,708
[45] Date of Patent: Nov. 17, 1998

[54] SULPHONAMIDES

[75] Inventors: Volker Breu, Schliengen, Germany; Kaspar Burri, Binningen, Switzerland; Jean-Marie Cassal, Mulhouse, France; Martine Clozel, St. Louis, France; Georges Hirth, Huningue, France; Bernd-Michael Löffler, Oberrimsingen, Germany; Marcel Müller, Frenkendorf, Switzerland; Werner Neidhart, Hagenthal le Bas, France; Henri Ramuz, Birsfelden, Switzerland

[73] Assignee: Hoffmann-La Roche Inc., Nutley, N.J.

[21] Appl. No.: 730,422

[22] Filed: Oct. 15, 1996

Related U.S. Application Data

[63] Continuation-in-part of Ser. No. 676,313, Jul. 18, 1996.

[30] Foreign Application Priority Data

Nov. 25, 1994 [CH]  Switzerland .............................. 3559/94
Jun. 6, 1995 [WO]  WIPO ..................... PCT/CH95/00131

[51] Int. Cl.⁶ ...................... C07D 239/69; C07D 401/12; C07D 403/12; A61K 31/505
[52] U.S. Cl. ................... 514/274; 514/227.8; 514/228.2; 514/228.5; 514/235.8; 514/236.5; 514/232.2; 514/232.5; 514/234.8; 514/234.5; 514/252; 514/249; 514/259; 514/262; 514/261; 514/269; 544/319; 544/238; 544/295; 544/296; 544/122; 544/123; 544/82; 544/58.6; 544/265; 544/276; 544/277; 544/284
[58] Field of Search ...................................... 544/319, 238, 544/122, 58.6, 277; 514/269, 274, 259, 234.5, 232.2, 228.5

[56] References Cited

U.S. PATENT DOCUMENTS 5,292,740   3/1994   Burri et al. .............................. 514/256

FOREIGN PATENT DOCUMENTS 526 708   2/1993   European Pat. Off. .

OTHER PUBLICATIONS

Burri et al., Chemical Abstract, vol. 120 (entry 217711) Apr. 25, 1994.

*Primary Examiner*—John M. Ford
*Attorney, Agent, or Firm*—George W. Johnston; William H. Epstein; John P. Parise

[57] ABSTRACT

Compounds of the formula

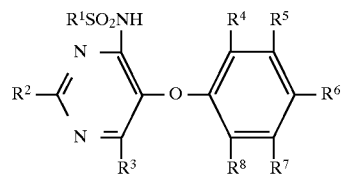

wherein the variables are hereinbelow defined. The compounds of formula I are inhibitors for endothelin receptors. They can be used for the treatment of disorders which are associated with endothelin activities, especially circulatory disorders such as hypertension, ischaemia, vasospasms and angina pectoris.

39 Claims, No Drawings

SULPHONAMIDES

This application is a CIP Application of Ser. No. 08/676,313, filed on Jul. 18, 1996.

SUMMARY OF THE INVENTION

The present invention is concerned with novel sulphonamides having the formula

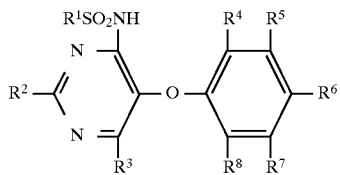

wherein

R$^1$ is heterocyclyl;

R$^2$ is selected from the group consisting of hydrogen, lower-alkyl, lower-alkoxy, lower-alkylthio, lower-alkoxy-lower-alkyl, lower-alkylsulphonyl-lower-alkoxy, phenyl, lower alkylphenyl, lower-alkoxyphenyl, lower-alkylenedioxyphenyl, phenyl-lower alkyl, lower alkyl-phenyl-lower alkyl, lower alkoxy-phenyl-lower alkyl, lower alkylenedioxyphenyl-lower alkyl, heterocyclyl and heterocycyl-lower alkyl;

R$^3$ is selected from the group consisting of lower-alkyl, lower-alkoxy, formyl, halo-lower-alkyl, hydroxy-lower-alkyl, amino-lower-alkyl, -CH$_2$O—A—lower—alkyl, —(CH$_2$)$_m$—O—(CR$^a$R$^b$)$_n$OH, —(CH$_2$)$_m$—O—(CR$^a$R$^b$)$_n$OR$^9$, —(CH$_2$)$_m$—O—(CR$^a$R$^b$)$_n$NH$_2$ and —(CH$_2$)$_m$—O—(CR$^a$R$^b$)$_n$—Y—R$^9$;

R$^4$–R$^8$ each are selected from the group consisting of hydrogen, lower-alkoxy and halogen;

R$^9$ is selected from the group consisting of heterocyclyl; phenyl; and phenyl substituted with a group selected from the group consisting of lower-alkyl, lower-alkoxy and halogen;

R$^a$ and R$^b$ each are hydrogen or lower-alkyl;

A is a ketalized 1,2-dihydroxy-ethylene group;

Y is selected from the group consisting of —OC(O)O—, —NH(C(O)NH— and —NHC(O)O—;

n is 2, 3 or 4; and m is 0 or 1.

The compounds of formula I inhibit endothelin binding and are therefore useful in the treatment of disorders associated with vasoconstriction, such as high blood pressure and coronary disorders.

DETAILED DESCRIPTION OF THE INVENTION

The present invention is concerned with novel sulphonamides and their use as medicaments. In particular, the invention is concerned with novel compounds of the formula

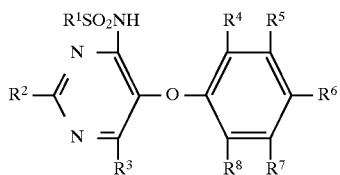

wherein

R$^1$ is heterocyclyl;

R$^2$ is selected from the group consisting of hydrogen, lower-alkyl, lower-alkoxy, lower-alkylthio, lower-alkoxy-lower-alkyl, lower-alkylsulphonyl-lower-alkoxy, phenyl, lower alkylphenyl, lower-alkoxyphenyl, lower-alkylenedioxyphenyl, phenyl-lower alkyl, lower alkyl-phenyl-lower alkyl, lower alkoxy-phenyl-lower alkyl, lower alkylenedioxyphenyl-lower alkyl, heterocyclyl and heterocycyl-lower alkyl;

R$^3$ is selected from the group consisting of lower-alkyl, lower-alkoxy, formyl, halo-lower-alkyl, hydroxy-lower-alkyl, amino-lower-alkyl, —CH$_2$O—A—lower—alkyl, —(CH$_2$)$_m$—O—(CR$^a$R$^b$)$_n$OH, —(CH$_2$)$_m$—O—(CR$^a$R$^b$)$_n$OR$^9$, —(CH$_2$)$_m$—O—(CR$^a$R$^b$)$_n$NH$_2$ and —(CH$_2$)$_m$—O—(CR$^a$R$^b$)$_n$—Y—R9;

R$^4$-R$^8$ each are selected from the group consisting of hydrogen, lower-alkoxy and halogen;

R$^9$ is selected from the group consisting of heterocyclyl; phenyl; and phenyl substituted with a group selected from the group consisting of lower-alkyl, lower-alkoxy and halogen;

R$^a$ and R$^b$ each are hydrogen or lower-alkyl;

A is a ketalized 1,2-dihydroxy-ethylene group;

Y is selected from the group consisting of —OC(O)O—, —O(C(O)NH—, —NH(C(O)NH—and —NHC(O)O—;

n is 2, 3 or 4; and m is 0 or 1.

The term "lower" used here denotes groups with 1–7 C atoms, preferably 1–4 C atoms. Alkyl, alkoxy and alkylthio groups as well as alkyl groups as components of alkanoyl groups can be straight-chain or branched. Methyl, ethyl, propyl, isopropyl, butyl, sec. and tert. butyl are examples of such alkyl groups. Halogen denotes fluorine, chlorine, bromine and iodine, with chlorine being preferred. A lower-alkylenedioxyphenyl residue is, for example, an ethylenedioxyphenyl residue. A ketalized 1,2-dihydroxyethylene group is, for example, the 2,2-dimethyl-1,3-dioxolan-4,5-diyl group. Examples of heterocyclyl residues are especially mono- or bicyclic which are mono- or disubstituted, e.g. by lower-alkyl, lower-alkanoyl, halogen, or by a further heterocyclic residue or unsubstituted and which have oxygen, nitrogen or sulphur as the hetero atom, such as 2- and 3-furyl, pyrimidinyl, 2-, 3- and 4-pyridyl, 1,2- and 1,4-diazinyl, morpholino, 2-and 3-thienyl, isoxazolyl, oxazolyl, thiazolyl, imidazolyl, pyrrolyl, benzofuranyl, benzothienyl, indolyl, purinyl, quinolyl, isoquinolyl and quinazolyl. Examples of heterocyclyl residues R$^1$ are especially substituted and unsubstituted pyridyl, pyrimidinyl, thienyl and isoxazolyl. Examples of heterocyclyl residues R$^2$ are especially pyrimidinyl and morpholino. Examples of heterocyclyl residues R$^9$ are especially pyridyl, pyrimidinyl and furyl.

Preferred compounds of formula I are those in which R$^1$ is a monocyclic, S-, N- and/or O-heterocyclic residue, especially pyridyl, pyrimidinyl, isoxazolyl, furyl or thienyl which is unsubstituted or substituted by lower-alkyl, halogen, amino, mono- or di-lower-alkylamino or lower-alkanoyl. Furthermore, there are preferred compounds of formula I in which R$^2$ is hydrogen, pyrimidinyl, pyridyl, morpholino, thiomorpholino, piperidino, pyrrolidino, benzodioxolyl, lower-alkoxyphenyl or lower-alkylthio and those in which R$^3$ is a residue —O—(CRaRb)nOH, —O—(CR$^a$R$^b$)$_n$NH$_2$ or a residue —O(CH$_2$)$_2$—Y—R$^9$, and R$^9$ is a monocyclic N—and/or 0—heterocyclic residue, especially pyridyl, pyrazinyl or furyl.

Of particular interest are compounds of formula I in which R$^1$ is a pyridyl residue substituted by lower-alkyl, R$^2$ is morpholino, $R^3$ is a residue —$O(CH_2)_2OC(O)NHR^9$, $R^4$ is lower-alkoxy and $R^5$–$R^8$ are hydrogen. Preferred residues $R^9$ are heterocyclyl residues, especially pyridyl residues such as 2-pyridyl.

The compounds of formula I given above are endothelin receptor inhibitors. They can therefore be used for the treatment of disorders which are associated with endothelin activities, especially circulatory disorders such as hypertension, ischaemia, vasospasms and angina pectoris.

The compounds of formula I can be manufactured by a) reacting a compound of the formula

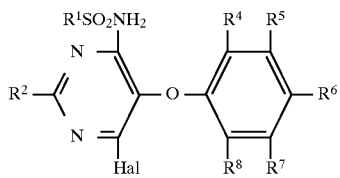

wherein $R^1$, $R^2$ and $R^4$–$R^8$ have the significance set forth above and

Hal is halogen, with a compound of the formula

wherein n, $R^a$ and $R^b$ have the significance set forth above and X represents O or NH, or b) reacting a compound of the formula

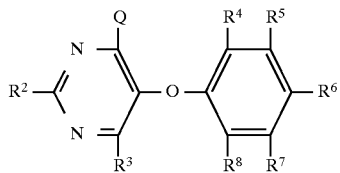

wherein $R^{2-R8}$ have the significance set forth above, with a compound of the formula

wherein $R^1$ has the significance set forth above and whereby Q represents halogen and Z represents amino or Q represents amino and Z represents halogen, or c) reacting a compound of the formula

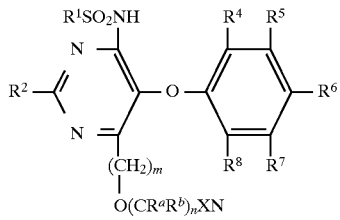

wherein $R^1$, $R^2$, $R^4$–$R^8$, $R^a$, $R^b$, X, m and n have the significance set forth above, c1) with an isocyanate of the formula $R^9NCO$ or a carbamoyl chloride of the formula $R^9NCOCl$, wherein $R^9$ has the significance set forth above, or c2) with phosgene and thereafter with an alcohol of the formula $R^9OH$; or with a chloroformate of the formula $R^9OC(O)Cl$; or d) reacting a compound of formula I in which $R^3$ represents halo-lower-alkyl with a compound of the formula

wherein A represents a ketalized 1,2-dihydroxy-ethylene group, and, if desired, modifying substituents present in the resulting compound of formula I and/or converting the compound of formula I obtained into a salt.

In the reaction of a compound of formula II with a compound of the formula $HO(CR^aR^b)_nXH$, this is conveniently used as the alkali metal alcoholate. The corresponding glycol or the corresponding aminoalcohol, thus e.g. ethylene glycol or aminoethanol, when n=2, is preferably used as the solvent. The alkali metal alcoholate is preferably sodium alcoholate. The reaction is conveniently carried out while heating, e.g. to 40°–120° C. In a preferred embodiment the compound $HO(CR^aR^b)_nXH$ is used as the monosodium salt of ethylene, propylene or butylene glycol or amino-ethanol, -propanol or -butanol.

The reaction of a compound of formula III with a compound of the formula $R^1SO_2Z$ can be carried out in a manner known per se for the manufacture of sulphonamides, e.g. in an inert organic solvent such as dimethyl sulphoxide, conveniently while heating and in a protective gas atmosphere, e.g. under argon.

The reaction in accordance with process variant c1) can be effected in a manner known per se preparation of carbamates and ureas from alcohols and, respectively, amines. Thus, a compound of formula IV can be converted into a compound of formula I in which Y is —OC(O)NH— with an isocyanate of the formula $R^9NCO$ in a suitable anhydrous organic solvent, e.g. a hydrocarbon such as toluene, conveniently while heating. The isocyanate can be generated in situ, e.g. from an azide of the formula $R^9CON_3$ by thermal decomposition. Likewise, compounds of formula I with Y=—NHC(O)NH—can be obtained using compounds of formula IV in which B is NH.

According to process variant c2) a compound of formula IV in which Y is oxygen can be reacted with phosgene and thereafter with an alcohol of the formula $R^9OH$ to give a compound of formula I in which A is a residue —OC(O) O—. A phosgene salt such as diphosgene (Cl—COOCCl$_3$) or triphosgene (CO(OCCl$_3$)$_2$ can be used in place of phosgene. Compounds of formula I with Y=—NHC(O)O— are obtained analogously starting from compounds of formula IV with Y=NH. The phosgene is conveniently used as a solution in an inert anhydrous organic solvent, e.g. a hydrocarbon such as toluene. The reaction with phosgene can be carried out at room temperature. The acid chloride obtained as an intermediate is reacted directly with the alcohol $R^9OH$, conveniently while heating.

The reaction in accordance with process variant d) can be carried out under the reaction conditions described for process variant a) and yields compounds of formula I in which $R^3$ is a residue —$CH_2O$—A-lower-alkyl.

Substituents present in the thus-obtained compound of formula I can be modified. Thus, a methyl group $R^3$ can be converted into a formyl group by oxidation. The oxidation can be carried out in a manner known per se, e.g. with selenium dioxide. The formyl group in the thus-obtained compound can be reduced to the hydroxymethyl group. This reduction can be carried out in a manner known per se, e.g. by means of reducing agents such as $NaBH_4$. The hydroxymethyl group can be converted into a halo-methyl group by reaction with a halogenating agent such as $POCl_3$/$PCl_5$. Furthermore, N-heterocyclic residues such as pyridile can be oxidized to N-oxides. All of these reactions can be carried out according to methods known per se. The compounds of formula I can be converted in a manner known per se into salts, e.g. alkali salts such as Na and K salts or alkaline earth metal salts such as Ca or Mg salts.

The compounds which are used as starting materials, insofar as they are not known or their preparation is described hereinafter, can be prepared in analogy to known methods or methods described in more details below.

The inhibitory activity of the compounds of formula I on endothelin receptors can be demonstrated using the test procedures described hereinafter:

I: Inhibition of endothelin binding to recombinant $ET_A$ receptors

A cDNA coding for human $ET_A$ receptors of human placenta was cloned (M. Adachi, Y.-Y. Yang, Y. Furuichi and C. Miyamoto, BBRC 180, 1265–1272) and expressed in the baculovirus-insect cell system. Baculovirus-infected insect cells from a 23 l fermenter are centrifuged off (3000× g, 15 minutes, 4° C.) 60 hours after the infection, re-suspended in Tris buffer (5 mM, pH 7.4, 1 mM $MgCl_2$) and again centrifuged. After a further re-suspension and centrifugation the cells are suspended in 800 ml of the same buffer and freeze-dried at −120° C. The cells disintegrate when the suspension in this hypotonic buffer mixture is thawed. After a repeated freeze-drying/thawing cycle the suspension is homogenized and centrifuged (25000× g, 15 minutes, 4° C.). After suspension in Tris buffer (75 mM, pH 7.4, 25 mM $MgCl_2$, 250 mM saccharose) 1 ml aliquots (protein content about 3.5 mg/ml) are stored at −85° C.

For the binding assay, the freeze-dried membrane preparations are thawed and, after centrifugation at 20° C. and 25000g for 10 minutes, re-suspended in assay buffer (50 mM Tris buffer, pH 7.4, containing 25 mM $MnCl_2$, 1 mM EDTA and 0.5% bovine serum albumin). 100 μl of this membrane suspension containing 70 μg of protein are incubated with 50 μl of $^{125}$I-endothelin (specific activity 2200 Ci/mMol) in assay buffer (25000 cpm, final concentration 20 pM) and 100 μl of assay buffer containing varying concentrations of test compound. The incubation is carried out at 20° C. for 2 hours or at 4° C. for 24 hours. The separation of free and membrane-bound radio-ligands is carried out by filtration over a glass fiber filter.

The inhibitory activity of compounds of formula I determined in this test procedure is given in Table 1 as the $IC_{50}$, i.e. as the concentration [nM] which is required to inhibit 50% of the specific binding of $^{125}$I-endothelin.

TABLE 1

| Compound of Example | $IC_{50}$ [nM] |
|---|---|
| 34 | 0.3 |
| 51 | 0.4 |

II. Inhibition of endothelin-induced contractions in isolated rat aorta rings

Rings with a length of 5 mm were cut out from the thorax aorta of adult Wistar-Kyoto rats. The endothelium was removed by lightly rubbing the internal surface. Each ring was immersed at 37° C. in 10 ml of Krebs-Henseleit solution in an isolated bath while gassing with 95% $O_2$ and 5% $CO_2$. The isometric stretching of the rings was measured. The rings were stretched to a pre-tension of 3 g. After incubation for 10 minutes with the test compound or vehicle cumulative dosages of endothelin-1 were added. The activity of the test compound was ascertained by the observed shift to the right of the dosage-activity curve of endothelin-1 in the presence of different concentrations of antagonist. This shift to the right (or "dose ratio", DR) corresponds to the quotient from the $EC_{50}$ values of endothelin-1 in the presence and in the absence of antagonist, with the $EC_{50}$ value denoting the endothelin concentration required for a half-maximum contraction.

The corresponding $PA_2$ value, which is a measure of the activity of the test compound, was calculated using a computer programmed according to the following equation from the "dose ratio" DR for each individual dosage-activity curve.

$pA_2$= log(DR-1)-log(antagonist-concentration)

The $EC_{50}$ of endothelin in the absence of test compounds is 0.3 nM.

The $pA_2$ values obtained with compounds of formula I are given in Table 2.

TABLE 2

| Compound of Example | Dose ratio (switch to the right) |
|---|---|
| 34 | 9.7 |
| 51 | 9.2 |

On the basis of their capability of inhibiting endothelin binding, the compounds of formula I can be used as medicaments for the treatment of disorders which are associated with vasoconstriction of increasing frequencies. Examples of such disorders are high blood pressure, coronary disorders, cardiac insufficiency, renal and myocardial ischaemia, renal insufficiency, dialysis, cerebral ischaemia, cerebral infarct, migraine, subarachnoid haemorrhage, Raynaud syndrome and pulmonary high pressure. They can also be used in atherosclerosis, the prevention of restenosis after balloon-induced vascular dilation, inflammations, gastric and duodenal ulcers, ulcus cruris, gram-negative sepsis, shock, glomerulonephritis, renal colic, glaucoma, asthma, in the therapy and prophylaxis of diabetic complications and complications in the administration of cyclosporin, as well as other disorders associated with endothelin activities.

The compounds of formula I can be administered orally, rectally, parentally, e.g. intravenously, intramuscularly, subcutaneously, intrathecally or transdermally; or sublingually or as opththalmological preparations, or as an areosol. Capsules, tablets, suspensions or solutions for oral administration, suppositories, injection solutions, eye drops, salves or spray solutions are examples of administration forms.

Intravenous, intramuscular or oral administration is a preferred form of use. The dosages in which the compounds of formula I are administered in effective amounts depend on the nature of the specific active ingredient, the age and the requirements of the patient and the mode of administration. In general, dosages of about 0.1–100 mg/kg body weight per day come into consideration. The preparations containing the compounds of formula I can contain inert or also pharmacodynamically active additives. Tablets or granulates e.g. can contain a series of binders, fillers, carriers or diluents. Liquid preparations can be present, for example, in the form of a sterile water-miscible solution. Capsules can contain a filler or thickener in addition to the active ingredient. Furthermore, flavor-improving additives as well as substances usually used as preserving, stabilizing, moisture-retaining and emulsifying agents as well as salts for varying the osmotic pressure, buffers and other additives can also be present.

The previously mentioned carrier materials and diluents can comprise organic or inorganic substances, e.g. water, gelatine, lactose, starch, magnesium stearate, talc, gum arabic, polyalkylene glycols and the like. It is a prerequisite that all adjuvants used in the manufacture of the preparations are non-toxic.

The following Examples illustrate the invention in more detail.

EXAMPLE 1

1.29 g of Na were dissolved in 50 ml of ethylene glycol at 50° C. Subsequently, 3.0 g of 5-tert-butyl-thiophene-2-sulphonic acid 6-chloro-5-(2-methoxy-phenoxy)-2,2'-bipyrimidin-4-ylamide were added portionwise at the same temperature and the mixture was heated at 100° C. for 4 ½ hours. The clear reaction solution was poured on to ice/dilute HCl solution and the mixture was extracted 3 times with 0.2l of ethyl acetate each time. The organic phase was washed 3 times with water, dried over sodium sulphate and finally evaporated on a rotary evaporator. 5-tert-Butyl-thiophene-2-sulphonic acid 6-(2-hydroxy-ethoxy)-5-(2-methoxy-phenoxy)-2,2'-bipyrimidin-4-ylamide was thus obtained as a pale yellow foam. MS: 493 (M-SO2).

Preparation of the starting compound a) 2.0 g of 5-tert-butyl-thiophene-2-sulphonyl chloride were dissolved in 30 ml of ethanol at room temperature, treated with 50 ml of 25% ammonia solution and heated at reflux for 4 ½ hours. The mixture was concentrated on a rotary evaporator, the residue was treated with water, extracted with ethyl acetate (150 ml), dried over magnesium sulphate and again concentrated on a rotary evaporator. There was thus obtained 5-tert-butyl-2-thiophene-2-sulphonamide as white crystals. MS: 219 (M). The potassium salt was obtained therefrom with K tert.-butylate in methanol.

b) 3.49 g of 4,6-dichloro-5-(2-methoxy-phenoxy)-2,2'-bipyrimidine were dissolved in 1 25 ml of dimethyl sulphoxide, 3.855 g of (5-tert-butyl-thiophene-2-sulphonamide) K were added at room temperature and the solution was subsequently stirred at room temperature for 20 hours. It was then treated with a further 1.285 g of (5-tert-butyl-thiophene-2-sulphonamide) K and left to react at room temperature for a further 2 hours. 200 ml of water [and] then 200 ml of ether were added to the reaction mixture while stirring vigorously, whereby a fine, white, crystalline precipitate formed and was filtered off under suction. The crystals were suspended in dilute, aqueous hydrochloric acid and stirred at room temperature for ½hour, filtered off under suction and dried in a high vacuum. There was thus obtained 5-tert-butyl-thiophene-2-sulphonic acid 6-chloro-5-(2-methoxy-phenoxy)-2,2'-bipyrimidin-4-ylamide as a white, crystalline solid. MS: 523.4 (M+H).

EXAMPLE 2

A solution of 3.23 g of 5-tert-butyl-thiophene-2-sulphonic acid 6-(2-hydroxy-ethoxy)-5-(2-methoxy-phenoxy)-2,2'-bipyrimidin-4-ylamide, 1.71 g of 2-pyridylcarboxylic acid azide and 70 mg of p-dimethylaminopyridine in toluene (50 ml) was heated at 80° C. for 2 hours. The toluene was removed on a rotary evaporator and the residue was partitioned between methylene chloride (0.5 l) and 1N HCl solution (0.35 l). The organic phase was dried over magnesium sulphate, the solvent was finally removed on a rotary evaporator. The crude product was chromatographed over silica gel with methylene chloride/MeOH (5/1) as the eluent. There was thus obtained pyridin-2-ylcarbamic acid 2-[6-(5-tert-butyl-thiophen-2-ylsulphonylamino)-5-(2-methoxy-phenoxy)-2,2'-bipyrimidin-4-yloxy]-ethyl ester as a pale yellow solid which was recrystallized from methylene chloride/MeOH. MS: 678.3 (M+H).

EXAMPLE 3

26 mg of sodium were dissolved in 2 ml of ethanolamine at 50° C., treated portionwise at the same temperature with 150 mg of the compound from Example 1, paragraph b), and the solution was heated at 100° C. for 4 hours. Subsequently, the mixture was poured on to ice/water, adjusted to pH 6 with 3N HCl, whereby there separated a pale yellow, crystalline solid which was filtered off under suction, washed with water and dried in a high vacuum. There was thus obtained 5-tert-butyl-thiophene-2-sulphonic acid 6-(2-amino-ethoxy)-5-(2-methoxy-phenoxy)-2,2'-bipyrimidin-4-ylamide as yellow crystals. MS: 557.4 (M+H).

EXAMPLE 4

100 mg of 5-tert-butyl-thiophene-2-sulphonic acid 6-(2-amino-ethoxy)-5-(2-methoxy-phenoxy)-2,2'-bipyrimidin-4-ylamide were dissolved in 10 ml of toluene, treated with 53 mg of 2-pyridylcarboxylic acid azide and the solution was heated at 120° C. for 4 hours. The toluene was removed on a rotary evaporator and the residue was partitioned between ethyl acetate and water. The organic phase was dried over magnesium sulphate and finally concentrated on a rotary evaporator. The residue was chromatographed on silica gel with methylene chloride/methanol (30/1) as the eluent. There was thus obtained 5-tert-butyl-thiophen-2-sulphonic acid 5-(2-methoxy-phenoxy)-6-[2-(3-pyridin-2-yl-ureido)-ethoxy]-2,2'-bipyrimidin-4-ylamide as a crystalline solid. MS: 677.4 (M+H).

EXAMPLE 5

92 mg of NaH (65%) were added at room temperature to a solution of 162.5 mg of 4-amino-6-methoxy-5-(2-methoxy-phenoxy)-2,2'-bipyrimidine in 10 ml of tetrahydrofuran, the solution was stirred at room temperature for 1½ hours and subsequently 162.5 mg of 5-tert-butyl-thiophene-2-sulphonyl chloride were added at the same temperature. The mixture was stirred at room temperature for a further 2 hours, poured on to ice/water, extracted with ethyl acetate, the aqueous phase was acidified and extracted with methylene chloride. The combined, organic phases were dried over magnesium sulphate and concentrated on a rotary evaporator. The residue was chromatographed over silica gel with methylene chloride/methanol (20/1) as the eluent. 5-tert-Butyl-N-[6-methoxy-5-(2-methoxy-phenoxy)-2,2'-bipyrimidin-4-yl]-thiophene-2-sulphonamide was obtained as a yellow powder. MS: 463 (M-SO2).

Preparation of the starting compounds a) 2.09 g of 4,6-dichloro-5-(2-methoxy-phenoxy)-2,2'-bipyrimidine (EP-A- 0 526 708) were suspended in 75 ml of methanol and 150 ml of ammonia were condensed at 75° C. using a feedpipe. The reaction mixture was left to come to room temperature overnight, concentrated in a water-jet vacuum and the residue was partitioned between a small amount of water and methylene chloride (500 ml). The organic phase was dried over sodium sulphate and concentrated on a rotary evaporator. The residue was triturated with ether, the resulting solid was separated and dried in a high vacuum. The 4-amino-6-chloro-5-(2-methoxy-phenoxy)-2,2'-bipyrimidine was thus obtained as a fine, almost white powder. MS: 329 (M).

b) 6.55 g of sodium methylate were added at room temperature to a solution of 4-amino-6-chloro-5-(2-methoxy-phenoxy)-2,2'-bipyrimidine in 200 ml of methanol and the solution was subsequently heated at reflux for 32 hours. The methanol was removed on a rotary evaporator, the residue was taken up in methylene chloride and washed with 1N hydrochloric acid. The organic phase was dried over magnesium sulphate, the solvent was finally removed in a water-jet vacuum. The crude product was chromatographed on silica gel with methylene chloride/ methanol (10/1) as the eluent. 4-Amino-6-methoxy-5-( 2-methoxy-phenoxy)-2,2'-bipyrimidine was obtained as a lemon-yellow powder MS: 325 (M).

EXAMPLE 6

In analogy to Example 1, from sodium glycolate and 5-pentyl-thiophene-2-sulphonic acid 6-chloro-5-(2-methoxy-phenoxy)-2,2'-bipyrimidin-4-ylamide there was obtained 5-pentyl-thiophene-2-sulphonic acid 6-(2-hydroxy-ethoxy)-5-(2-methoxy-phenoxy)-2,2'-bipyrimidin-4-ylamide as a white solid. MS: 570.3 (M+H).
Preparation of the starting compounds:

a) (5-n-Pentyl-thiophene-2-sulphonamide) K was obtained from 2-pentyl-5-(t-butylsulphonamido)thiophene (EP-A- 0 512 675) with ethanol/conc. HCl and salt formation with potassium tert.-butylate in methanol.

b) Analogously to Example 1, paragraph b), by reacting (5-n-pentyl-thiophene-2-sulphonamide) K and 4,6-dichloro-5-(2-methoxy-phenoxy)-2,2'-bipyrimidine there was obtained 5-pentyl-thiophene-2-sulphonic acid 6-chloro-5-(2-methoxy-phenoxy)-2,2'-bipyrimidin-4-ylamide as a white solid. MS: 545 (M).

EXAMPLE 7

Analogously to Example 2, from 2-pyridylcarboxylic acid azide and 5-pentyl-thiophene-2-sulphonic acid 6-(2-hydroxy-ethoxy)-5-(2-methoxy-phenoxy)-2,2'-bipyrimidin-4-ylamide there was obtained pyridin-2-ylcarbamic acid 2-[5-(2-methoxy-phenoxy)-6-(5-pentyl-thiophen-2-ylsulphonylamino)-2,2'-bipyrimidin-4-yloxy]-ethyl ester as a white solid. MS: 692.4 (M+H).

EXAMPLE 8

In analogy to Example 2, from sodium glycolate and 5-(2,2-dimethyl-propionyl)-thiophene-2-sulphonic acid 6-chloro-5-( 2-methoxy-phenoxy)-2,2'-bipyrimidin-4-ylamide there was obtained 5-(2,2-dimethyl-propionyl)-thiophene-2-sulphonic acid 6-(2-hydroxy-ethoxy)-5-(2-methoxy-phenoxy)-2,2'-bipyrimidin-4-ylamide as a pink powder. MS: 586.3 (M+H).
Preparation of the starting compound a) Analogously to Example 1, paragraph b), by reacting the potassium salt of 5-(2,2-dimetylpropanoyl)thiophene-2-sulphonamide (preparation: J Org. Chem., Vol 56, 4260) and 4,6-dichloro-5-( 2-methoxy-phenoxy)-2,2'-bipyrimidine there was obtained 5-(2, 2-dimethyl-propionyl)-thiophene-2-sulphonic acid 6-chloro-5-(2-methoxy-phenoxy)-2, 2'-bipyrimidin-4-ylamide as a crystalline solid. MS: 560.1 (M+H). The potassium salt was obtained therefrom with potassium tert.-butylate in methanol.

EXAMPLE 9

Analogously to Example 2, from 2-pyridylcarboxylic acid azide and 5-(2,2-dimethyl-propionyl)-thiophene-2-sulphonic acid 6-(2-hydroxy-ethoxy)-5-(2-methoxy-phenoxy)-2,2'-bipyrimidin-4-ylamide there was obtained the desired pyridin-2-ylcarbamic acod 2-[6-[5-(2, 2-dimethylpropionyl)-thiophen-2-ylsulphonylamino]-5-(2-methoxy-phenoxy))- 2,2'-bipyrimidin-4-yloxy]-ethyl ester as a beige powder. MS: 704.3 (M+H).

EXAMPLE 10

1.75 g of Na were dissolved in 70 ml of ethylene glycol at 50° C. Subsequently, 4.9 g of 5-isopropyl-pyridine-2-sulphonic acid 6-chloro-5-(2-methoxy-phenoxy)-2,2'-bipyrimidin-4-ylamide were added portionwise at the same temperature and the mixture was heated to 100° C. for 4 hours. The clear reaction solution was poured into 200 ml of water, brought to pH 1 with 3N HCl, the separated yellow crystals (sic) were filtered off under suction, washed with water, then with ether and finally dried in a high vacuum. There was thus obtained 5-lsopropyl-pyridine-2-sulphonic acid 6-(2-hydroxy-ethoxy)-5-(2-methoxy-phenoxy)-2,2'-bipyrimidin-4-ylamide as a yellow, crystalline solid. MS: 537.3 (M–H).
Preparation of the starting compounds a) 4.0 g of 5-isopropylpyridine-2-sulphonamide were dissolved in 40 ml of MeOH, 2.308 g of potassium tert.-butylate were added at room temperature and the solution was stirred for a further 20 minutes. Subsequently, it was concentrated completely on a rotary evaporator and the thus-obtained potassium salt was dried in a high vacuum.

b) 3.49 g of 4,6-dichloro-5-(2-methoxy-phenoxy)-2,2'-bipyrimidine were dissolved in 125 ml of dimethyl sulphoxide, 4.7 g of (5-isopropyl-pyridine-2-sulphonamide) K were added at room temperature and the solution was subsequently stirred at room temperature for 20 hours. It was poured into 350 ml of water and 90 ml of ether while stirring vigorously, the solution was brought to pH 1 by the addition of 3N HCl. The white, crystalline precipitate was filtered off under suction and washed with water, then ether. The crystals were suspended in dilute, aqueous hydrochloric acid (100 ml of water and 50 ml of 1N HCl) and stirred for 5 minutes, filtered off under suction and again washed with water and dried in a high vacuum. There was thus obtained 5-isopropyl-pyridine-2-sulphonic acid 6-chloro-5-(2-methoxy-phenoxy)-2,2'-bipyrimidin-4-ylamide as a white, crystalline solid. MS: 511.3 (M–H).

EXAMPLE 11

2.0 g of 5-isopropyl-pyridine-2-sulphonic acid 6-(2-hydroxy-ethoxy)-5-(2-methoxy-phenoxy)-2,2'-bipyrimidin-4-ylamide were dissolved in 80 ml of toluene, treated with 1.1 g of 2-pyridylcarboxylic acid azide and the solution was subsequently heated at 90° C. for 4 hours. It was concentrated on a rotary evaporator and the residue was partitioned between 1 N HCl and ethyl acetate. The organic phase was dried over magnesium sulphate, the solvent was removed in a water-jet vacuum and the residue was chromatographed on silica gel with methylene chloride/methanol (30/1) as the eluent. There was thus obtained pyridin-2-ylcarbamic acid 2-[6-(5-isopropyl-pyridin-2-ylsulphonylamino)-5-(2-methoxy-phenoxy)-2, 2'-bipyrimidin-4-yloxy]-ethyl ester as yellow crystals. MS: 657.3 (M+H).

For the preparation of the dihydrochloride, the compound was dissolved in methylene chloride and treated with the corresponding amount of 4.4N HCl in ethanol at room temperature. The solution was concentrated on a rotary evaporator, the separated, crystalline solid was isolated and dried in a high vacuum at 60° C. for 4 hours.

EXAMPLE 12

In analogy to Example 4, from 5-isopropyl-pyridine-2-sulphonic acid 6-(2-amino-ethoxy)-S-(2-methoxy-phenoxy)-2, 2'-bipyrimidin-4-ylamide and 2-pyridylcarboxylic acid azide there was obtained the desired 5-isopropyl-pyridine-2-sulphonic acid 5-(2-methoxy-phenoxy)-6-[2-(3-pyridin-2-yl-ureido)-ethoxy]-2,2'-bipyrimidin-4-ylamide as yellow crystals. MS: 656.3 (M–H).

The starting compound was obtained analogously to Example 3 from ethanolamine and the compound from Example 10, paragraph b), as a yellow foam. MS: 538.3 (M+H).

EXAMPLE 13

In analogy to Example 10, from pyridine-2-sulphonic acid 6-chloro-5-(2-methoxy-phenoxy)-2,2'-bipyrimidin-4-ylamide and ethylene glycol there was pyridine-2-sulphonic acid 6-(2-hydroxy-ethoxy)-5-(2-methoxy-phenoxy)-2,2'-bipyrimidin-4-ylamide as white crystals. MS: 615.4 (M–H).

Preparation of the starting compounds a) 1.7 g of 2-pyridylsulphonyl chloride (J Org. Chem., Vol. 54, 389) were dissolved in 30 ml of ethanol, 30 ml of 25% ammonia solution were added while cooling with ice and the mixture was subsequently heated at reflux for 4 hours. The reaction solution was concentrated on a rotary evaporator, the residue was partitioned between ethyl acetate and water, the organic phase was dried over magnesium sulphate and finally concentrated on a rotary evaporator, the 2-pyridylsulphonamide separating as a beige, crystalline solid. MS: 469.2 (M–H). The K salt was obtained therefrom with K tert.-butylate in methanol.

b) Analogously to Example 10, paragraph b), by reacting (2-pyridylsulphonamide)-K and 4,6-dichloro-5-(2-methoxy-phenoxy)-2, 2'-bipyrimidine there was obtained pyridine-2-sulphonic acid 6-chloro-5-(2-methoxy-phenoxy)-2,2'-bipyrimidin-4-ylamide as white crystals. MS: 495.3 (M–H).

EXAMPLE 14

In analogy to Example 11, from pyridine-2-sulphonic acid 6-(2-hydroxy-ethoxy)-5-(2-methoxy-phenoxy)-2,2'-bipyrimidine-4-ylamide and 2-pyridylcarboxylic acid azide there was obtained pyridin-2-ylcarbamic acid 2-[5-(2-methoxy-phenoxy)-6-pyridin-2-1sulphonylamino)-2,2'-bipyrimidin-4-yloxy]-ethyl ester as white crystals. MS: 615.4 (M–H)

EXAMPLE 15

In analogy to Example 10, from pyridine-3-sulphonic acid 6-chloro-5-(2-methoxy-phenoxy)-2,2'-bipyrimidin-4-ylamide and ethylene glycol there was obtained pyridine-3-sulphonic acid 6-(2-hydroxy-ethoxy)-5-(2-methoxy-phenoxy)-2,2'-bipyrimidin-4-ylamide as white crystals. MS: 496 (M).

Preparation of the starting compounds a) In analogy to Example 13, paragraph a), from 3-pyridylsulphonyl chloride (J Org. Chem., Vol. 54, 389) and ammonia there was obtained 2-pyridylsulphonamide as a white, crystalline solid, the potassium salt being obtained therefrom with potassium tert.-butylate in methanol.

b) Analogously to Example 10, paragraph b), by reacting (3-pyridylsulphonamide)-K and 4,6-dichloro-5-(2-methoxy-phenoxy)-2, 2'-bipyrimidine there was obtained the desired pyridine-3-sulphonic acid 6-chloro-5-(2-methoxy-phenoxy)-2,2'-bipyrimidin-4-ylamide as white crystals. MS: 470 (M).

EXAMPLE 16

In analogy to Example 11, from pyridine-3-sulphonic acid 6-(2-hydroxy-ethoxy)-5-(2-methoxy-phenoxy)-2,2'-bipyrimidin-4-ylamide and 2-pyridylcarboxylic acid azide there was obtained pyridin-2-ylcarbamic acid 2-[5-(2-methoxy-phenoxy)-6-pyridin-3-ylsulphonylamino)-2,2'-bipyrimidin-4-yloxy]-ethyl ester as white crystals. MS: 615.4(M–H).

EXAMPLE 17

213 mg of 6-[2-(tert-butyl-dimethyl-silanoxy)-ethoxy]-5-(2-chloro-5-methoxy-phenoxy)-pyrimidin-4-ylamine were dissolved in 15 ml of tetrahydrofuran, treated at room temperature with 92 mg of NaH (65%), stirred at room temperature for 2 hours and then 155 mg of 5-tert-butyl-thiophene-2-sulphonyl chloride were added portionwise. The solution was stirred at room temperature for a further 2 hours, poured into ice-water and extracted twice with a total of 200 ml of ethyl acetate. After usual working-up of the organic phase the silyl-protected crude product was chromatographed on silica gel with methylene chloride/ethyl acetate (8/1) as the eluent.

The brownish foam obtained (219 mg) was dissolved in 15 ml of acetonitrile, treated at room temperature with 1.5 ml of HF solution (40%) and stirred for 2 hours. The reaction mixture was partitioned between ethyl acetate and semi-saturated NaCl solution and the organic phase was worked-up as usual. The crude product was chromatographed on silica gel with methylene chloride/ethyl acetate (4/1) as the eluent and recrystallized from ether/hexane. There was thus obtained 5-tert-butyl-thiophene-2-sulphonic acid 5-(2-chloro-5-methoxy-phenoxy)-6-(2-hydroxy-ethoxy)-pyrimidin-4-ylamide as white crystals. MS: 449 (M-SO2)

Preparation of the starting compound a) 3-Methoxyphenol was converted with sulphuryl chloride into 2-chloro-5-methoxyphenol according to the procedure of M. Julia and l. de Rosnay, Chimie Thérapeutique 5 (1969), 334.

b) 18.2 g of 2-chloro-5-methoxyphenol were dissolved in 150 ml of dry methanol. 9.3 g of MeONa were added, followed by 25 g of dimethyl chloromalonate. The reaction mixture was stirred at 50° C. for 2 hours. After distillation of the solvent the residue was partitioned between toluene and $H_2O$ in a separating funnel and washed neutral. After crystallization in ethanol there was obtained (2-chloro-5-methoxy)phenoxy-dimethylmalonate, white crystals with m.p. 68°–69° C.

c) 1.43 g of Na were dissolved in 70 ml of MeOH. Then, 5.8 g of (2-chloro-5-methoxy)phenoxy-dimethylmalonate, and 2.29 g of formamidine acetate were added; the reaction mixture was stirred under reflux for 1.5 hours. Then, the solvent was distilled off, the residue was taken up in $H_2O$, the aqueous phase was extracted with ethyl acetate, the organic phase was discarded and the aqueous phase was acidified to pH 4 with acetic acid, the 5-(2-chloro-5-methoxy) phenoxy-4,6(1 H,5H)-pyrimidinedione separating as a white powder. MS: m/e=268 (M).

d) A mixture of 3.75 g of 5-(2-chloro-5-methoxy) phenoxy-4,6(1 H,5H)-pyrimidinedione, 5.4 g of N-ethyldiisopropylamine, 12.5 ml of $POCl_3$ in 20 ml of dioxan was stirred under reflux for 18 hours. After distillation of the volatile components the residue was partitioned between ethyl acetate and $H_2O$ and washed neutral. After distillation of the solvent the compound was purified on silica gel with $CH_2Cl_2$ as the eluent. 4,6-Dichloro-5-(2-chloro-5-methoxy-phenoxy)-pyrimidine was obtained as white crystals with m.p. 88°–89° C. after crystallization from EtOH.

e) About 500 ml of $NH_3$ were conducted at −78° C. into a solution of 9.9 g of 4,6-dichloro-5-(2-chloro-5-methoxy-phenoxy)-pyrimidine from Example 1e) in 400 ml of ethanol. Thereafter, the reaction mixture was stirred at −78° C. for 15 hours and at room temperature for 50 hours and finally evaporated. The residue was partitioned between ethyl acetate and water and the organic phase was worked-up. 8.53 g of 6-chloro-5-(2-chloro-5-methoxy-phenoxy)-pyrimidin-4-ylamine were thus obtained as yellow crystals. MS: 285 (M).

f) 8.53 of the previously obtained compound were added to a solution of 0.82 g of sodium in 100 ml of ethylene glycol at 50° C. The solution was heated to 100° C. for 20 hours, thereafter partitioned between semi-saturated NH₄Cl solution and CH₂Cl₂ and worked-up. There were obtained 8.3 g of 2-[6-amino-5-(2-chloro-5-methoxy-phenoxy)-4-pyrimidin-4-yloxy]-1-ethanol as a white solid, which was silylated without further purification. For this purpose, the above material (8.3 g) was dissolved in 300 ml of methylene chloride, treated with 8.15 g of dimethylaminopyridine and finally at room temperature with 10.05 g of t-butyldimethylchlorosilane. The reaction solution was stirred at room temperature for 5 hours. Then, it was filtered, the solution was concentrated, the evaporation residue was partitioned between semi-saturated NH₄Cl solution and ethyl acetate and the organic phase was worked-up. Subsequent crystallization from methylene chloride/hexane yielded 7 g of 6-[2-(tert-butyl-dimethyl-silanyloxy)-ethoxy]-5-(2-chloro-5-methoxy-phenoxy)-pyrimidin-4-ylamine. MS: 410 (M—CH₃).

EXAMPLE 18

In analogy to Example 2, from 5-tert-butyl-thiophene-2-sulphonic acid 5-(2-chloro-5-methoxy-phenoxy)-6-(2-hydroxy-ethoxy)-pyrimidin-4-ylamide and 2-pyridylcarboxylic acid azide there was obtained pyridine-2-ylcarbamic acid 2-[6-(5-tert-butyl-thiophen-2-ylsulphonylamino)-5-(2-chloro-5-methoxy-phenoxy)-pyrimidin-4-yloxy]-ethyl ester as white crystals. MS: 634.3 (M+H).

EXAMPLE 19

In analogy to Example 2, from the compound of Example 17 and 4-pyridylcarboxylic acid azide there was obtained pyridin-4-ylcarbamic acid 2-[6-(5-tert-butyl-thiophen-2-ylsulphonylamino)-5-(2-chloro-5-methoxy-phenoxy)-pyrimidin-4-yloxy]-ethyl ester as white crystals. MS: 634.3 (M+H).

EXAMPLE 20

In analogy to Example 17, using 6-[2-(tert-butyl-dimethyl-silanoxy)-ethoxy]-5-(2-methoxy-phenoxy)-pyrimidin-4-ylamine as the reaction component, there was obtained 5-tert-butyl-thiophene-2-sulphonic acid 6-(2-hydroxy-ethoxy)-5-(2-methoxy-phenoxy)-pyrimidin-4-ylamide as a white solid. MS: 479 (M).

EXAMPLE 21

180 mg of the compound from the foregoing step were added to a Na glycolate solution from 1.5 ml of ethylene glycol and 46 mg of Na. 1 ml of DMSO was added in order to complete the dissolution. The mixture was left to react at 90° C. for 3 hours. After cooling to room temperature the reaction medium was acidified to pH 4 with aqueous citric acid and the compound formed was subsequently extracted with ethyl acetate. After distillation of the ethyl acetate the N-[5-(2-chloro-5-methoxy-phenoxy)-6-(2-hydroxy-ethoxy)-pyrimidin-4-yl]-5-isopropyl-pyridine-2-sulphonamide was crystallized from ethanol. There were obtained 175 mg of white crystals which decomposed at 180° C.
Preparation of the starting compound 306 mg of 4,6-dichloro-5-(2-chloro-5-methoxy-phenoxy)-pyrimidine, 320 mg of 5-isopropyl-2-pyridine-sulphonamide and 180 mg of K tert.butylate dissolved in 2 ml of DMSO were reacted at 90° C. for 3 hours. After cooling to room temperature the reaction medium was acidified with aqueous citric acid; the compound was extracted with ethyl acetate and, after distillation of the solvent, crystallized from ethanol. 250 mg of N-[6-chloro-5-(2-chloro-5-methoxy-phenoxy)-pyrimidin-4-yl]-5-isopropyl-pyridine-sulphonamide were obtained as white crystals with m.p. 174°–175° C.

EXAMPLE 22

100 mg of N-[5-(2-chloro-5-methoxy-phenoxy)-6-(2-hydroxy-ethoxy)-pyrimidin-4-yl]-5-isopropyl-pyridine-2-sulphonamide and 38.5 mg of 2-pyridyl-carboxylic acid azide were dissolved in 1 ml of dry dioxan. The solution was stirred at 95° C. for 2 hours, whereby N₂ was liberated. After distillation of the solvent the compound was crystallized from ethanol. 115 mg of pyridin-2-yl-carbamic acid 2-[5-(2-chloro-5-methoxy-phenoxy)-6-(5-isopropyl-pyridin-2-ylsulphonylamino)-pyrimidin-4-yloxy]-ethyl ester were obtained as white crystals with m.p. 190°–191° C.

EXAMPLE 23

5-Isopropyl-N-[6-(2-hydroxy-ethoxy)-5-(2-methoxy-phenoxy)-2-(3-methoxy-phenyl)-pyrimidin-4-yl]-pyridine-2-sulphonamide. m.p. 139°–140° C. (from ethanol), was obtained in analogy to Example 21.
Preparation of the starting compound 400 mg of N-[6-chloro-5-(2-methoxy-phenoxy)-2-(3-methoxy-phenyl)-pyrimidin-4-yl]-5-isopropyl-pyridine-2-sulphonamide were obtained from 330 mg of 4,6-dichloro-2-(3-methoxy-phenyl)-5-(2-methoxy-phenoxy)-pyrimidine and 420 mg of (5-isopropyl-pyridine-2-sulphonamide) K in analogy to Example 21, second paragraph.

EXAMPLE 24

In analogy to Example 22, from 115 mg of 5-isopropyl-N-[6-(2-hydroxy-ethoxy)-5-(2-methoxy-phenoxy)-2-(3-methoxy-phenyl)-pyrimidin-4-yl]-pyridine-2-sulphonamide and 38.5 mg of 2-pyridyl-carboxylic acid azide there were obtained 120 mg of pyridin-2-yl-carbamic acid 2-[6-(5-isopropyl-pyridin-2-ylsulphonylamino)-5-(2-methoxy-phenoxy)-2-(3-methoxy-phenyl)-pyrimidin-4-yloxy]-ethyl ester. M.p. 158°–160° C. (from ethanol).

EXAMPLE 25 a) N-[6-Chloro-5-(2-methoxy-phenoxy)-2-methylsulphanyl-pyrimidin-4-yl]-5-isopropyl-pyridine-2-sulphonamide was obtained from 4,6-dichloro-2-methylsulphanyl-5-(2-methoxy-phenoxy)-pyrimidine and (5-isopropyl-pyridine-2-sulphonamide) K in analogy to Example 21. M.p. 192° C. (from ethanol).

b) The compound was converted with Na glycolate into 5-isopropyl-N-[6-(2-hydroxy-ethoxy)-5-(2-methoxy-phenoxy)-2-methylsulphanyl-pyrimidin-4-yl]-pyridine-2-sulphonamide. M.p. 76°–78° C. (from EtOH).

EXAMPLE 26

106 mg of pyridin-2-ylcarbamic acid 2-[6-(5-isopropyl-pyridin-2-ylsulphonylamino)-5-(2-methoxy-phenoxy)-2-methylsulphanyl-pyrimidin-4-yloxy]-ethyl ester were obtained from 100 mg of 5-isopropyl-N-[6-(2-hydroxy-ethoxy)-5-(2-methoxy-phenoxy)-2-methylsulphanyl-pyrimidin-4-yl]-pyridine-2-sulphonamide and 2-pyridylcarboxylic acid azide in analogy to Example 22. M.p. 213°–214° C. (from ethanol).

EXAMPLE 27 a) N-[6-Chloro-2-(1,3-benzodioxol-5-yl)-5-(2-methoxy-phenoxy)-pyrimidin-4-yl]-5-isopropyl-pyridine-2- sulphonamide was obtained from 4,6-dichloro-2-(1,3-benzodioxol-5-yl)-5-(2-methoxy-phenoxy)-pyrimidine and (5-isopropyl-pyridine-2-sulphonamide) K.

b) This compound was converted with Na glycolate into N-[2-(1,3-benzodioxol-5-yl)-6-(2-hydroxy-ethoxy)-5-(2-methoxy-phenoxy)-25 pyrimidin-4-yl]-5-isopropyl-pyridine-2-sulphonamide. M.p. 184° C. (from EtOH).

EXAMPLE 28

110 mg of pyridin-2-ylcarbamic acid 2-[2-(1,3-benzodioxol-5-yl)-6-(5-isopropyl-pyridin-2-ylsulphonylamino)-5-(2-methoxy-phenoxy)-pyrimidin-4-yloxy]-ethyl ester were obtained from 116 mg of N-[2-( 1,3-benzodioxol-5-yl)-6-(2-hydroxy-ethoxy)-5-(2-methoxy-phenoxy)-pyrimidin-4-yl]-5-isopropyl-pyridine-2-sulphonamide and 2-35 pyridyl-carboxylic acid in analogy to Example 22. M.p. 184° C. (from ethanol).

EXAMPLE 29 a) N-[6-Chloro-5-(2-chloro-5-methoxy-phenoxy)-2-morpholin-4-yl-pyrimidin-4-yl]-5-isopropyl-pyridin-2-sulphonamide was obtained from 4.6-dichloro-2-morpholin-4-yl-pyrimidine and (5-isopropyl-pyridine-2-sulphonamide) K.

b) Reaction of this compound with Na glycolate yielded N-[5-(2-10 chloro-5-methoxy-phenoxy)-6-(2-hydroxy-ethoxy)-2-morpholin-4-yl-pyrimidin-4-yl]-5-isopropyl-pyridine-2-sulphonamide. M.p. 189°–190° C. (from EtOH).

EXAMPLE 30

116 mg of N-[5-(2-chloro-5-methoxy-phenoxy)-6-(2-hydroxy-ethoxy)-2-morpholin-4-yl-pyrimidin-4-yl]-5-isopropyl-pyridine-2-sulphonamide were converted with 2-pyridyl-carboxylic acid azide into pyridin-2-ylcarbamic acid 2-[5-(2-chloro-5-methoxy-phenoxy)-6-(5-isopropyl-pyridin-2-ylsulphonylamino)-2-morpholin-4-ylpyrimidin-4-yloxy]-ethyl ester in analogy to Example 22. From ethanol there were obtained 106 mg of white crystals which decomposed at 240° C.

EXAMPLE 31

5-Methyl-pyridine-2-sulphonic acid 6-(2-hydroxy-ethoxy)-5-(2-methoxy-phenoxy)-2,2'-bipyrimidin-4-ylamide, m.p. 190° C. (from ethanol), was obtained from 5-methyl-pyridine-2-sulphonic acid [6-chloro-5-(2-methoxy-phenoxy)-2,2'-bipyrimidin-4-yl]-amide and Na glycolate in analogy to Example 21.
Preparation of the starting compound
a) 2-Amino-5-methylpyridine was diazotized and converted into 2-bromo-5-methylpyridine according to the procedure of F.H. Case (JACS 68 (1946), 2574).

b) 4.8 g of this compound in 40 ml of propylene glycol were reacted with 7.4 g of sodium hydrogen sulphide at 150° C. After cooling to room temperature 5 ml of acetic acid were added dropwise to the reaction mixture, the 2-mercapto-5-methylpyridine formed separating as a yellow powder.

c) 50 ml of a 1.2 molar sodium hypochlorite solution were added dropwise within 30 minutes to a two-phase mixture of 40 ml of $CH_2Cl_2$, 20 ml of 37% aqueous HCl and 3 g of 2-mercapto-5-methylpyridine cooled to −10° C. Subsequently, the organic phase was extracted three times with $H_2O$. The 5-methylpyridine sulphochloride was obtained as a yellowish liquid after distillation of the solvent.

d) Reaction of the sulphochloride with 25% $MH_4OH$ solution gave 5-methylpyridine-2-sulphonamide.

e) 0.7 g of 4,6-dichloro-5-(2-methoxy-phenoxy)-2,2'-bipyrimidine, 520 mg of 5-methylpyridine-2-sulphonamide and 320 mg of K tert. butylate dissolved in 2 ml of DMSO were stirred at 80° C. for 3 hours. After usual working-up of the reaction mixture 410 mg of 5-methyl-pyridine-2-sulphonic acid [6-chloro-5-(2-methoxy-phenoxy)-2,2'-bipyrimidin-4-yl]-amide were obtained.

EXAMPLE 32

In analogy to Example 22, from 105 mg of 5-methyl-pyridine-2-sulphonic acid 6-(2-hydroxy-ethoxy)-5-(2-methoxy-phenoxy)-2, 2'-bipyridmin-4-ylamide and 30 mg of 2-pyridyl-carboxylic acid azide there were obtained 100 mg of pyridin-2-ylcarbamic acid 2-[5-(2-methoxy-phenoxy)-6-(5-methyl-pyridin-2-ylsulphonylamino)-2,2'-bipyridimin-4-yloxy]-ethyl ester as beige crystals. M.p: decomposition at 198° C.

EXAMPLE 33 a) In analogy to Example 22, from 712 mg of 4,6-dichloro-5-(2-methoxy-phenoxy)-2-morpholin-4-yl-pyrimidine and (5-methyl-pyridine-2-sulphonamide) K there were obtained 580 mg of 5-methyl-pyridine-2-sulphonic acid 6-chloro-5-(2-methoxy-phenoxy)-2-morpholin-4-yl-pyrimidin-4-ylamide.

b) Reaction of this compound with Na glycolate gave 5-methyl-pyridine-2-sulphonic acid 6-(2-hydroxy-ethoxy)-5-(2-methoxy-phenoxy)-2-morpholin-4-yl-pyrimidin-4-ylamide. M.p. 195°–196° C. (from ethanol).

EXAMPLE 34

117 mg of pyridin-2-yl-carbamic acid 2-[5-(2-methoxy-phenoxy)-6-(5-methyl-pyridin-2-ylsulphonylamino)-2-morpholin-4-yl-pyrimidin-4-yloxy]-ethyl ester were obtained from 105 mg of 5-methyl-pyridine-2-sulphonic acid 6-(2-hydroxy-ethoxy)-5-(2-methoxy-phenoxy)-2-morpholin-4-yl-pyrimidin-4-ylamide and 2-pyridyl-carboxylic acid azide in analogy to Example 22. M.p: decomposition at 175° C.

EXAMPLE 35

105 mg of 5-methyl-pyridine-2-sulphonic acid 6-(2-hydroxy-ethoxy)-5-(2-methoxy-phenoxy)-2-morpholin-4-yl-pyrimidin-4-ylamide in 2 ml of dichloromethane was treated with 3 ml of a 1.9 molar phosgene solution in toluene. After 1 hour at room temperature the chloroformate had formed completely. Then, the excess reagent was distilled off; the residue was taken up in a mixture of chloroform and pyridine; 0.5 g of 3-(hydroxymethyl)-furan was added and the mixture was left to react at 60°C for 3 hours. After the usual working-up the compound was purified on silica gel (dichloromethane-diethyl ether 4:1 by vol. as the eluent). 65 mg of carboxylic acid furan-3-ylmethyl ester 2-[5-(2-methoxy-phenoxy)-6-(5-methyl-pyridin-2-sulphonylamino)-2-morpholin-4-yl-pyrimidin-4-yloxy]-ethyl ester, MS: 640.5 [M–H)−], were obtained.

EXAMPLE 36

9.2 g of 4-[4-chloro-5-(2-chloro-5-methoxy-phenoxy)-6-methyl-pyrimidin-2-yl]-morpholine and 17.8 g of 5-isopropyl-pyridine-2-sulphonamide potassium in 130 ml of dry dimethyl sulphoxide were heated to 120° C. under argon for 16 hours. Thereafter, the dimethyl sulphoxide was distilled off, the residue was partitioned between ethyl acetate and 1 N hydrochloric acid and the organic phase was washed neutral. The organic phase was dried, the solvent was evaporated and the residue was recrystallized from ethanol. 10.3 g of 5-isopropyl-pyridine-2-sulphonic acid 5-(2-chloro-5-methoxy-phenoxy)-6-methyl-2-morpholin-4-yl-pyrimidin-4-ylamide, MS: M =534, were obtained.

EXAMPLE 37

1 g of the compound obtained in Example 36 and 2.1 g of selenium dioxide in 40 ml of dioxan were stirred in an autoclave at 170° C. for 7 hours. The reaction mixture was filtered and the filtrate was concentrated. The residue was partitioned between ethyl acetate and water. The organic phase was dried, the solvent was evaporated and the residue was purified over silica gel with ethyl acetate/hexane. 0.53 g of 5-isopropyl-pyridine-2-sulphonic acid 5-(2-chloro-5-methoxy-phenoxy)-6-formyl-2-morpholin-4-yl-pyrimidin-4-ylamide, m.p. 194° C., was obtained.

EXAMPLE 38

0.1 g of the compound obtained in Example 37 in 3 ml of ethanol was treated with 0.014 g of sodium borohydride. The reaction mixture was stirred at 80° C. for 1 hour. Thereafter, the ethanol was distilled off and the residue was partitioned between chloroform and 1 N HCl. The organic phase was washed with water and dried, the solvent was evaporated and the residue was chromatographed over silica gel with chloroform-methanol. After recrystallization from dichloromethane-ethanol there was obtained 0.072 g of 5-isopropyl-pyridine-2-sulphonic acid 5-(2-chloro-5-methoxy-phenoxy)-6-hydroxymethyl-2-morpholin-4-yl-pyrimidin-4-ylamide. M.p. 105° C.

EXAMPLE 39

0.2 g of the compound obtained in Example 38 in 3.5 ml of $POCl_3$ was stirred with 0.083 g of $PCl_5$ at 20° C. for 2 hours. Thereafter, the $POCl_3$ was distilled off and the residue was partitioned between ethyl acetate and aqueous sodium bicarbonate (sic). The organic phase was washed with water, dried and the solvent was evaporated. The residue was chromatographed over silica gel with chloroform-methanol, thereafter recrystallized from dichloromethane-ethanol. 0.150 g of 5-isopropyl-pyridine-2-sulphonic acid 5-(2-chloro-5-methoxy-phenoxy)-6-chloromethyl-2-morpholin-4-yl-pyrimidin-4-ylamide, m.p. 205° C., was obtained.

EXAMPLE 40

0.130 g of the compound obtained in Example 39 was added to a sodium glycolate solution from 0.35 g of ethylene glycol and 0.021 g of sodium. The reaction mixture was stirred at 80° C. under argon for 2 hours. Thereafter, the ethylene glycol was distilled off and the residue was partitioned between ethyl acetate and 1N hydrochloric acid. The organic phase was washed with water, dried over sodium sulphate and the solvent was distilled off. The residue was recrystallized in ether-petroleum ether. 0.104 g of 5-(2-chloro-5-methoxy-phenoxy)-6-(2-hydroxy-ethoxymethyl)-2-morpholin-4-yl-pyrimidin-4-ylamide, m.p. 166° C., was obtained.

EXAMPLE 41

Pyridin-2-ylcarbamic acid 2-[5-(2-chloro-5-methoxy-phenoxy)-6-(5-isopropyl-pyridine-2-sulphonylamino)-2-morpholin-4-yl-pyrimidin-yl-methoxy]-ethyl ester, MS: $(M-H)^-=713$, was obtained in analogy to Example 2 from the compound obtained in Example 40.

EXAMPLE 42

Pyridin-2-ylcarbamic acid 5-(2-chloro-5-methoxy-phenoxy)-6-(5-isopropyl-pyridin-2-ylsulphonylamino)-2-morpholin-4-yl-pyrimidin-4-ylmethyl ester, MS: (M-H)-=669 was obtained in analogy to Example 2 from the compound obtained in Example 38.

EXAMPLE 43

5-lsopropyl-pyridine-2-sulphonic acid (RS)-5-(2-chloro-5-methoxy-phenoxy)-6-(2,2-dimethyl-1,3-dioxolan-3-ylmethoxymethyl)-2-morpholin-4-yl-pyrimidin-4-ylamide, MS: $(M-H)^-=663$, was obtained in analogy to Example 40 from the compound obtained in Example 39 and (RS)-2,2-dimethyl-1,3-dioxolan-4-methanol Na.

EXAMPLE 44

A solution of 0.05 g of the compound prepared in Example 43 in 2 ml of dioxan was treated with 2 ml of 1 N HCl and heated to 80° C. for 15 minutes. After evaporation the residue was chromatographed over silica gel with chloroform-methanol and yielded 5-isopropyl-pyridine-2-sulphonic acid (RS)-5-(2-chloro-5-methoxy-phenoxy)-6-(2,3-dihydroxy-propoxymethyl)-2-morpholin-4-yl-pyrimidin-4-ylamide. M.p. 116° C., MS: $(M-H)^-=623$.

EXAMPLE 45

345 mg of sodium were dissolved in 50 ml of abs. ethylene glycol at 80° C. The solution was left to cool somewhat and 1.56 g of 5-isopropyl-pyridine-2-sulphonic acid 6-chloro-5-(2-methoxy-phenoxy)-2-morpholin-4-yl-pyrimidin-4-ylamide were added. The resulting solution was stirred at 140° C. for 24 hours, the solvent was removed in a high vacuum and the residue was dissolved in 40 ml of water. After 4 hours at 5° C. the mixture was suction filtered, the crystals were suspended in 40 ml of water, covered with ethyl acetate and treated dropwise while stirring with 1N aqueous HCl until the pH had fallen to 3.5. The aqueous phase was extracted three times with ethyl acetate and the organic phases were washed twice with water and once with saturated NaCl solution. The combined organic phases were dried and concentrated until crystallization occurred (about 5 ml). The crystals were filtered off under suction, washed with ether and dried. There were obtained 1.144 g (70%) of white crystals of 5-isopropyl-pyridine-2-sulphonic acid 6-(2-hydroxy-ethoxy)-5-(2-methoxy-phenoxy)-2-morpholin-4-yl-pyrimidin-4-ylamide, m.p. 157°–160° C., MS: $(M-H)^-=544.4$.

Preparation of the starting compound

A solution of 1.18 g of 4,6-dichloro-5-(2-methoxy-phenoxy)-2-morpholin-4-yl-pyrimidine and 2.12 g (8.88 mmol) of 5-isopropyl-pyridine-2-sulphonamide potassium salt in 25 ml of dry DMSO was heated to 80° C. for 3 hours until the dichloride had disappeared completely. The DMSO was removed in a high vacuum, the residue was taken up with 60 ml of water and the aqueous solution was washed three times with diethyl ether. The solution was then acidified to pH 3.5 with 1N HCl and the product was extracted three times with ethyl acetate. The organic phases were washed twice with water and finally once with saturated sodium chloride solution, combined, dried with sodium sulphate and evaporated. The crystalline residue was digested twice with absolute diethyl ether in order to completely remove a trace of 5-isopropyl-pyridine-2-sulphonamide. The crystals remaining behind were filtered off and dried. There were obtained 1.66 g (96%) of 5-isopropyl-pyridine-2-sulphonic acid 6-chloro-5-(2-methoxy-phenoxy)-2-morpholin-4-yl-pyrimidin-4-ylamide as white crystals of m.p. 168°–176° C., MS: (M–H)⁻=518.3.

EXAMPLE 46

5-tert.Butylthiophene-2-sulphonic acid 6-(2-hydroxy-ethoxy)-5-(2-methoxy-phenoxy-2-morpholin-4-yl-pyrimidin-4-ylamide was obtained as a white solid foam in 54% yield, MS: 565.5 (M+H)⁺, in analogy to Example 45 after a reaction period of 10 hours at 120° C. with the addition of DMSO as the solubilizer (ethylene glycol:DMSO 5:2).

EXAMPLE 47

2,5-Dichlorothiophene-3-sulphonic acid 6-(2-hydroxy-ethoxy)-5-(2-methoxy-phenoxy)-2-morpholin-4-yl-pyrimidin-4-ylamide was obtained as white crystals in 43% yield in analogy to Example 45 after a reaction period of 3 hours at 140° C. MS: 575.3 (M–H)⁻.

EXAMPLE 48

3,5-Dimethylisoxazole-4-sulphonic acid 6-(2-hydroxy-ethoxy)-5(2-methoxy-phenoxy)-2-morpholin-4-yl-pyrimidin-4-ylamide, white crystals of m.p. 144°–147° C., MS: 520.4 (M–H)⁻, was obtained in analogy to Example 45 after a reaction period of 3.5 hours at 140° C.

EXAMPLE 49

110 mg of sodium were dissolved in 2.5 ml of ethylene glycol at 50° C. The solution was left to cool to room temperature and 260 mg of 2,5-dichlorothiophene-3-sulphonic acid 6-chloro-5-(2-methoxy-phenoxy)-2,2'-bipyrimidin-4-ylamide were added. After heating to 50° C. for 2 hours the glycol was removed in a high vacuum and the solid residue was dissolved in 20 ml of water. The product was precipitated by adding 0.3 ml of acetic acid. After filtration, washing with water and drying at 50° C. in a high vacuum 182 mg (67%) of pale beige crystals of 2,5-dichlorothiophene-3-sulphonic acid 6-(2-hydroxy-ethoxy)-5-(2-35 methoxy-phenoxy)-2,2'-bipyrimidin-4-ylamide, m.p. 157°–160° C., MS: M+(569), 470 (M⁺–(SO₂+Cl)), were obtained.

Preparation of the starting compound

A solution of 0.349 g of 4,6-dichloro-5-(2-methoxy-phenoxy)-2,2'-bipyrimidine and 0.405 g of 2,5-dichlorothiophene-3-sulphonamide potassium salt in 5 ml of dry DMSO was held at room temperature for 16 hours. Thereafter, 0.112 g of K tert.-butylate was added, whereupon the reaction had finished within 5 hours. The reaction mixture was poured on to 40 ml of ice-water and extracted with 40 ml of diethyl ether in order to remove excess reagent. From the aqueous phase by salting-out with saturated sodium chloride solution (20 ml) there was obtained 2,5-dichlorothiophene-3-sulphonic acid 6-chloro-5-(2-methoxy-phenoxy)-2,2'-bipyrimidin-4-ylamide, [which was isolated] by filtration and washing with ether (0.54 g of beige powder).

In order to obtain the free sulphonamide, the Na salt was suspended in water and the suspension was acidified with acetic acid and extracted with ethyl acetate to which a small amount of CH₂Cl₂ had been added. The organic phase was washed twice with saturated sodium chloride solution, dried with MgSO₄ and evaporated under reduced pressure. The residue was washed briefly with diethyl ether and hexane and then dried. There was obtained 0.30 g (54%) as a beige powder of m.p. 140° C. (dec.). MS: 444 (M–(SO₂+Cl)).

In analogy, using 3,5-dimethylisoxazolyl-4-sulphonamide potassium there was obtained 3,5-dimethylisoxazole-4-sulphonic acid 6-chloro-5-(2-methoxy-phenoxy)-2,2'-bipyrimidin-4-ylamide in 71 % yield as a beige, slightly reddish powder of m.p. 184°–187° C. MS: M+=488, 393 (M–(SO₂+OCH₃)).

EXAMPLE 50

3,5-Dimethyl-isoxazole-4-sulphonic acid 6-(2-hydroxy-ethoxy)-5-(2-methoxy-phenoxy)-2,2'-bipyrimidin-4-ylamide was obtained as a beige powder of m.p. 200°–204° C., MS: 514 (M⁺), 450 (M⁺–SO₂), 419 (450-CH₃O), in analogy to Example 49.

EXAMPLE 51

A solution of 888 mg of pyridine-2-carbonyl azide in 15 ml abs. dioxan was held at 80° C. for 15 minutes. The solution was left to cool somewhat, 1.09 g of the compound prepared in Example 45 were added and the solution was held at 90° C. for 4 hours. Thereafter, it was evaporated to dryness, the residue was taken up with ethyl acetate, washed twice with water and once with saturated sodium chloride solution, the organic phases were combined, dried and concentrated, whereby crystals of the product separated. For definitive purification, it was chromatographed on silica gel with EtOAc/CH₂Cl₂ (1:1) and there were obtained 931 mg (70%) of white crystals of pyridin-2-ylcarbamic acid 2-[6-(5-isopropyl-pyridin-2-ylsulphonylamino)-5-(2-methoxy-phenoxy)-2-morpholin-4-yl-pyrimidin-4-yloxy]ethyl ester of m.p. 200°–202° C. MS: 664.4 (M–H)–. IR (KBr) 1 730 cm⁻¹ (carbamate).

EXAMPLE 52

Pyridin-2-ylcarbamic acid 2-[6-( 2,5-dichlorothiophen-3-ylsulphonylamino)-5-(2-methoxy-phenoxy)-2,2'-bipyrimidin-4-yloxy]ethyl ester was obtained as white crystals of m.p.194°–197° C., MS: 690.1 (M+H)+, IR (KBr) 1732 cm⁻¹ (carbamate), in 61% yield in analogy to Example 51 from the compound prepared in Example 49.

EXAMPLE 53

Pyridin-2-ylcarbamic acid 2-[5-(2-methoxy-phenoxy)-6-(3, 5-dimethyl-isoxazol-4-ylsulphonylamino)-2,2'-bipyrimidin-4-yloxy]ethyl ester was obtained as pale yellow crystals of m.p. 217°–218° C., MS: 635.3 (M+H)⁺, IR (KBr) 1736 cm⁻¹ (carbamate), was obtained in 68% yield in analogy to Example 51 from the compound prepared in Example 50.

EXAMPLE 54

Pyridin-2-ylcarbamic acid 2-[6-(5-tert-butylthiophen-2-ylsulphonylamino)-5-(2-methoxy-phenoxy)-2-morpholin-4-yl-pyrimidin-4-yloxy]-ethyl ester was obtained as a white foam, MS: 683.5 (M–H)⁻, in 90% yield in analogy to Example 51 from the compound prepared in Example 46.

EXAMPLE 55

Pyridin-2-ylcarbamic acid 2-[6-(2, 5-dichloro-thiophen-3-ylsulphonylamino)-5-(2-methoxy-phenoxy)-2-morpholin-4-yl-pyrimidin-4-yloxy]-ethyl ester, white crystals of m.p.

194°–196° C., MS: 695.3 (M–H)⁻, was obtained in 55% yield in analogy to Example 51 from the compound prepared in Example 47.

EXAMPLE 56

Pyridin-2-ylcarbamic acid 2-[6-(3, 5-dimethyl-isoxazol-4-ylsulphonylamino)-5-(2-methoxy-phenoxy)-2-morpholin-4-yl-pyrimidin-4-yloxy]-ethylester, white crystals of m.p. 106°–109° C., MS: 640.4 (M–H)⁻, was obtained in 70% yield in analogy to Example 51 from the compound prepared in Example 48.

EXAMPLE 57

5-lsopropyl-pyridine-2-sulphonic acid 6-(2-hydroxy-ethoxy)-5-(2-methoxy-phenoxy)-2-morpholin-4-yl-pyrimidin-4-ylamide (54.5 mg) was dissolved in N,N-dimethylacetamide (5 ml). 14.4 mg of 60% NaH suspension were added at room temperature and the mixture was stirred for 20 minutes. Finally, 2-chloropyrimidine (11.7 mg) was added. The reaction mixture was stirred for 18 hours at room temperature and poured into ice water. Saturated NH₄Cl solution was added and the mixture was extracted with ethyl acetate. The organic phase was washed with water, dried over magnesium sulphate and evaporated. The residue was chromatographed over silica gel using methylene chloride/methanol (100/1) as the eluent. There was obtained 5-isopropyl-pyridine-2-sulphonic acid {5-(2-methoxy-phenoxy)-2- morpholin-4-yl-6-[2-(pyrimidin-2-yloxy)-ethoxy]-pyrimidin-4-yl }-amide as white crystals. MS: 624 (M+H)

EXAMPLE 58 a) In analogy to Example 45, by reacting 5-isopropyl-pyridine-2-sulphonic acid [6-chloro-2-(3-methoxy-benzyl)-5-(2-methoxy- phenoxy)-pyrimidin-4-yl]-amide with Na in ethylene glycol there was obtained 5-isopropyl-pyridine-2-sulphonic acid [6-(2-hydroxy-ethoxy)-2-(3-methoxy-benzyl)-5-(2-methoxy-phenoxy)-pyrimidin-4-yl]-amide as a white foam. MS: 579.3 (M–H)
Preparation of the starting material
b) 10.8 g of 3-methoxyphenylacetonitrile were dissolved in ethanol (100 ml) and the solution was saturated with hydrogen chloride at room temperature. The mixture was subsequently stirred for 12 hours a room temperature, the solution was cooled to 0° C. and the precipitated crystals were sucked off. The crude product was recrystallized from acetone/diethyl ether. There was thus obtained 2-(3-methoxy-phenyl)-acetimidic acid ethyl ester hydrochloride as a white crystalline solid. MS: 193 (M)
c) 2-(3-Methoxy-phenyl)-acetimidic acid ethyl ester hydrochloride (12 g) was dissolved in ethanol (100 ml) and treated at -75° C. with 14 ml of liquid ammonia. The mixture was left to come to room temperature within 5 hours and was then evaporated in a rotary evaporator. The residue was suspended in acetone and the precipitated crystals were sucked off and dried under a high vacuum. There was thus obtained 2-(3-methoxy-phenyl)-acetamidine hydrochloride as a white crystalline solid. MS: 164 (M)
d) Na (2.3 g) was dissolved in methanol (40 ml) and 2-(3-methoxy-phenyl)-acetamidine hydrochloride (10 g) and (2-methoxyphenoxy)-malonic acid dimethyl ester (12.67 g) were added in succession at room temperature. The mixture was stirred for 5 hours at room temperature, concentrated in a rotary evaporator and the crude product was added to water. The aqueous phase was washed with ethyl acetate, adjusted to pH 1 and the precipitated crystals were sucked off and dried under a high vacuum. There was thus obtained 2-(3-methoxy-benzyl)-5-(2-methoxy-phenoxy)-pyrimidine-4,6-diol as beige crystals. MS: 354 (M)
e) 2-(3-Methoxy-benzyl)-5-(2-methoxy-phenoxy)-pyrimidine-4,6-diol (14 g) was dissolved in acetonitrile (150 ml). Collidine (5.24 ml) and phosphorus oxychloride (21.7 ml) were added at room temperature and the mixture was stirred for 9 hours at room temperature. The mixture was poured into ice water and extracted with ethyl acetate. The organic phase was washed with semi-saturated KHCO₃ solution, dried over magnesium sulhate and evaporated. The residue was taken up in hexane/diethyl ether, filtered and the filtrate was evaporated in a rotary evaporator. There was thus obtained 4,6-dichloro-2-(3-methoxy-benzyl)-5-(2-methoxy-phenoxy)-pyrimidine as light brown crystals. MS: 390 (M)
f) In analogy to Example 45, by reacting 4,6-dichloro-2-(3-methoxy-25 benzyl)-5-(2-methoxy-phenoxy)-pyrimidine with potassium 5-isopropyl-pyridine-2-sulphonamide there was obtained 5-isopropyl-pyridine-2-sulphonic acid [6-chloro-2-(3-methoxy-benzyl)-5-(2-methoxy-phenoxy)-pyrimidin.-4-yl]-amide as a yellow foam. MS: 553.1 (M–H)

EXAMPLE 59 a) In analogy to Example 45, by reacting 5-isopropyl-pyridine-2-sulphonic acid [6-chloro-2-.(3-methoxy-benzyl)-5-phenoxy-pyrimidin-35 4-yl]-amide with Na in ethylene glycol there was obtained 5-isopropyl-pyridine-2-sulphonic acid [6-(2-hydroxy-ethoxy)-2-(3-methoxy-benzyl)-5-phenoxy-pyrimidin-4-yl]-amide as light yellow crystals. MS: 549.2 (M–H)
Preparation of the starting material
b) In analogy to Example 58d, by condensing 2-(3-methoxy-phenyl)-acetamidine hydrochloride with phenoxy-malonic acid dimethyl ester there was obtained 2-(3-methoxy-benzyl)-5-phenoxypyrimidine-4, 6-1o diol as a yellow foam. MS: 324 (M)
c) In analogy to Example 58e, by chlorinating 2-(3-methoxy-benzyl)-5-phenoxypyrimidine-4,6-diol with phosphorus oxychloride there was obtained 4,6-dichloro-2-(3-methoxy-benzyl)-5-phenoxy-pyrimidine as yellow crystals. MS: 360 (M)
d) In analogy to Example 45, by reacting 4,6-dichloro-2-(3-methoxy-benzyl)-5-phenoxy-pyrimidine with potassium 5-isopropyl-pyridine-2-sulphonamide there was obtained 5-isopropyl-pyridine-2-sulphonic acid [6-chloro-2-(3-methoxy-benzyl)-5-phenoxy-pyrimidin-4-yl]-amide as a yellow foam. MS: 523 (M–H)

EXAMPLE 60

5-lsopropyl-pyridine-2-sulphonic acid [6-(2-hydroxy-ethoxy)-2-(3-methoxy-benzyl)-5-phenoxy-pyrimidin-4-yl]-amide (55 mg) was dissolved in dry methylene chloride (3 ml). Boron tribromide (50 mg ) in methylene chloride (2 ml) was added at 0° C. The mixture was stirred for 2 hours at 0° C. and for a for a further 4 hours at room temperature, evaporated in a rotary evaporator and the residue was chromatographed over silica gel using methylene chloride/ethyl acetate as the eluent. 35 There was obtained 5-isopropyl-pyridine-2-sulphonic acid [2-(3 -hydroxy-benzyl)-6-(2-hydroxy-ethoxy)-5-phenoxy-pyrimidin-4-yl]-amide as white crystals. MS: 525.1 (M–H)

EXAMPLE A

Tablets containing the following ingredients can be produced in a conventional manner:

| Ingredients | Per tablet |
| --- | --- |
| Compound of formula I | 10.0–100.0 mg |
| Lactose | 125.0 mg |
| Corn starch | 75.0 mg |
| Talc | 4.0 mg |
| Magnesium stearate | 1.0 mg |

EXAMPLE B

Capsules containing the following ingredients can be produced in a conventional manner:

| Ingredients | Per capsule |
| --- | --- |
| Compound of formula I | 25.0 mg |
| Lactose | 150.0 mg |
| Corn starch | 20.0 mg |
| Talc | 5.0 mg |

EXAMPLE C

| | |
| --- | --- |
| Compound of formula I | 3.0 mg |
| Gelatine | 150.0 mg |
| Phenol | 4.7 mg |
| Water for injection | ad 1.0 ml |

EXAMPLE D 500 mg of compound of formula I are suspended in 3.5 ml of Myglyol 812 and 0.08 g of benzyl alcohol. This suspension is filled into a container having a dosage valve. 5.0 g of Freon 12 are filled into the container under pressure through the valve. The Freon is dissolved in the Myglyol-benzyl alcohol mixture by shaking. This spray container contains about 100 single doses which can be applied individually.

We claim:

1. A compound of the formula:

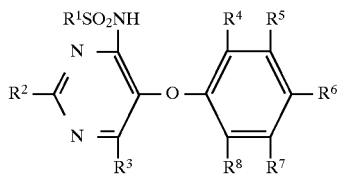

wherein $R^1$ is a heterocyclyl selected from the group consisting of unsubstituted 2-furyl, 3-furyl, pyrimidinyl, 2-pyridyl, 3-pyridyl, 4-pyridyl, 1,2-diazinyl, 1,4-diazinyl, morpholino, 2-thienyl, 3-thienyl, isoxazolyl, oxazolyl, thiazolyl, imidazolyl, pyrrolyl, benzofuranyl, benzothienyl, indolyl, purinyl, thiomorpholino, piperidino, quinolyl, isoquinolyl and quinazolyl; or heterocyclyl mentioned above mono- or disubstituted with $C_{1-7}$-alkyl, $Cl_{-1-7}$-alkanoyl, halogen, amino, mono-$C_{1-7}$-alkyl amino, or di-$C_{1-7}$-alkyl amino;

$R^2$ is selected from the group consisting of hydrogen, $C_{1-7}$-alkyl, $C_{1-7}$-alkoxy, $C_{1-7}$-alkylthio, $C_{1-7}$-alkoxy-$C_{1-7}$-alkyl, $C_{1-7}$-alkylsulphonyl-$C_{1-7}$-alkoxy, phenyl, $C_{1-7}$-alkoxy-phenyl, $C_{1-7}$-alkylenedioxyphenyl, and a heterocyclyl selected from the group consisting of unsubstituted 2-furyl, 3-furyl, pyrimidinyl, 2-pyridyl, 3-pyridyl, 4-pyridyl, 1,2-diazinyl, 1,4-diazinyl, morpholino, 2-thienyl, 3-thienyl, isoxazolyl, oxazolyl, thiazolyl, imidazolyl, pyrrolyl, benzofuranyl, benzothienyl, indolyl, purinyl, thiomorpholino, piperidino, quinolyl, isoquinolyl and quinazolyl; or heterocyclyl mentioned above mono- or disubstituted with $C_{1-7}$-alkyl, $C_{1-7}$-alkanoyl, halogen, amino, mono-$C_{1-7}$-alkylamino, or di-$C_{1-7}$-alkylamino;

$R^3$ is selected from the group consisting of $C_{1-7}$-alkyl, $C_{1-7}$-alkoxy, formyl, halo-$C_{1-7}$-alkyl, hydroxy-$C_{1-7}$-alkyl, amino-$C_{1-7}$-alkyl, —CH$_2$O—A—C$_{1-7}$-alkyl, —(CH$_2$)$_m$—O—(CR$^a$R$^b$)$_n$OH, —(CH$_2$)$_m$—O—(CR$^a$R$^b$)$_n$NH$_2$ and —(CH$_2$)$_m$—O—(CR$^a_R$$^b$)$_n$—Y—R$^9$;

$R^4$–$R^8$ each are selected from the group consisting of hydrogen, $C_{1-7}$-alkoxy and halogen;

$R^9$ is a heterocyclyl selected from the group consisting of unsubstituted 2-furyl, 3-furyl, pyrimidinyl, 2-pyridyl, 3-pyridyl, 4-pyridyl, 1,2-diazinyl, 1,4-diazinyl, morpholino, 2-thienyl, 3-thienyl, isoxazolyl, oxazolyl, thiazolyl, imidazolyl, pyrrolyl, benzofuranyl, benzothienyl, indolyl, purinyl, thiomorpholino, piperidino, quinolyl, isoquinolyl, and quinazolyl; or heterocyclyl mentioned above mono- or disubstituted with $C_{1-7}$-alkyl, $C_{1-7}$-alkanoyl, halogen, amino, mono-$C_{1-7}$-alkylamino, or di-$C_{1-7}$; and phenyl substituted with the group selected from the group consisting of $C_{1-7}$-alkyl, $C_{1-7}$-alkoxy, halogen and $C_{1-7}$-alkyl;

$R^a$ and $R^b$ each are hydrogen or $C_{1-7}$-alkyl;

A is a ketalized 1,2-dihydroxy-ethylene group;

Y is selected from the group consisting of —OC(O)O—, —O(C(O)NH—, —NH(C(O)NH— and —NHC(O)O—;

n is 2, 3 or 4; and m is 0 or 1.

2. The compound of claim 1, wherein $R^2$ is selected from the group consisting of hydrogen, pyrimidinyl, pyridyl, morpholino, thiomorpholino, piperidino, pyrrolidino, benzodioxolyl, $C_{1-7}$-alkoxyphenyl, and $C_{1-7}$-alkylthio.

3. The compound of claim 1, wherein $R^3$ is a residue selected from the group consisting of —O—(CR$^a$R$^b$)$_n$OH, —O—(CR$^a$R$^b$)$_n$NH$_2$ and —O(CH$_2$)$_2$—Y—R$^9$, and R$^9$ is 2-furyl, 3-furyl, pyrimidinyl, 2-pyridyl, 3-pyridyl, 4-pyridyl, 1,2-diazinyl, morpholino, isoxazolyl, oxazolyl, imidazolyl, pyrrolyl, or piperidino.

4. The compound of claim 3, wherein $R^3$ is a residue —O(CH$_2$)$_2$—Y—R$^9$ and Y is —(O)C(O)NH—.

5. The compound of claim 3, wherein $R^3$ is a residue —O(CH$_2$)$_2$—Y—R$^9$ and Y is —(O)C(O)O—.

6. The compound of claim 3, wherein $R^3$ is a residue —O(CH$^2$)$_2$—Y—R$^9$ and Y is —NHC(O)NH—.

7. The compound of claim 1, wherein $R^3$ is selected from the group consisting of $C_{1-7}$-alkyl, $C_{1-7}$-alkoxy, formyl, halo-$C_{1-7}$-alkyl, hydroxy-$C_{1-7}$-alkyl and —CH$_2$O—A—C$_{1-7}$-alkyl.

8. The compound of claim 3, wherein $R^9$ is selected from the group consisting of pyridyl, pyrazinyl, and furyl.

9. The compound of claim 1, wherein $R^3$ is hydroxyethoxy.

10. The compound of claim 9, wherein the compound is selected from the group consisting of 5-tert-butyl-thiophene-2-sulphonic acid 6-(2-hydroxyethoxy)-5-(2-methoxy-phenoxy)-2,2'-bipyrimidin-4-ylamide, 5-pentyl-thiophene-2-sulphonic acid 6-(2-hydroxy-ethoxy)-5-(2-methoxy-phenoxy)-2,2'-bipyrimidin-4-ylamide, 5-(2,2-dimethyl-propionyl)-thiophene-2-sulphonic acid 6-(2-hydroxy-ethoxy)-5-(2-methoxy-phenoxy)-2,2'-bipyrimidin-4-ylamide, 5-isopropyl-pyridine-2-sulphonic acid 6-(2-hydroxy-ethoxy)-5-(2-methoxy-phenoxy)-2,2'-bipyrimidin-4-ylamide, pyridine-3-sulphonic acid 6-(2-hydroxy-ethoxy)-5-(2-methoxy-phenoxy)-2,2'-bipyrimidin-4-ylamide, 5-tert-butyl-thiophene-2-sulphonic acid 5-(2-chloro-5-methoxy-phenoxy)-6-(2-hydroxy-ethoxy)-pyrimidin-4-ylamide, 5-tert-butyl-thiophene-2-sulphonic acid 6-(2-hydroxy-ethoxy)-5-(2-methoxy-phenoxy)-pyrimidin-4-ylamide, N-[5-(2-chloro-5-methoxy-phenoxy)-6-(2-hydroxy-ethoxy)-pyrimidin-4-yl]-5-isopropyl-pyridine-2-sulphonamide, 5-isopropyl-N-[6-(2-hydroxy-ethoxy)-5-(2-methoxy-phenoxy)-2-(3-methoxy-phenyl)-pyrimidin-4-yl]-pyridine-2-sulphonamide, 5-isopropyl-N-[6-(2-hydroxy-ethoxy)-5-(2-methoxy-phenoxy)-2-methylsulphanyl-pyrimidin-4-yl]-pyridine-2-sulphonamide, N-[2-( 1 , 3-benzodioxol-5-yl)-6-(2-hydroxy-ethoxy)-5-(2-methoxy-phenoxy)-pyrimidin-4-yl]-5-isopropyl-pyridine-2-sulphonamide, N-[5-(2-chloro-5-methoxy-phenoxy)-6-(2-hydroxy-ethoxy)-2-morpholin-4-yl-pyrimidin-4-yl]-5-isopropyl-pyridine-2-sulphonamide, 5-methyl-pyridine-2-sulphonic acid 6-(2-hydroxy-ethoxy)-5-(2-methoxy-phenoxy)-2,2'-bipyrimidin-4-ylamide, 5-methyl-pyridine-2-sulphonic acid 6-(2-hydroxy-ethoxy)-5-(2-methoxy-phenoxy)- 2-morpholin-4-yl-pyrimidin-4-ylamide, 5-isopropyl-pyridine-2-sulphonic acid 6-(2-hydroxy-ethoxy)-5-(2-methoxy-phenoxy)-2-morpholin-4-yl-pyrimidin-4-ylamide, 5-tert.butylthiophene-2-sulphonic acid 6-(2-hydroxy-ethoxy)-5-(2-methoxy-phenoxy-2-morpholin-4-yl-pyrimidin-4-ylamide, 2,5-dichlorothiophene-3-sulphonic acid 6-(2-hydroxy-ethoxy)-5-(2-methoxy-phenoxy)-2-morpholin-4-yl-pyrimidin-4-ylamide, 3,5-dimethylisoxazole-4-sulphonic acid 6-(2-hydroxy-ethoxy)-5-(2-methoxy-phenoxy)-2-morpholin-4-yl-pyrimidin-4-ylamide, 2,5-dichlorothiophene-3-sulphonic acid 6-(2-hydroxy-ethoxy)-5-(2-methoxy-phenoxy)-2,2'-bipyrimidin-4-ylamide, and 3,5-dimethyl-isoxazole-4-sulphonic acid 6-(2-hydroxy-ethoxy)-5-(2-methoxy-phenoxy)-2,2'-bipyrimidin-4-ylamide.

11. The compound of claim 1, wherein $R^3$ is aminoethoxy.

12. The compound of claim 11, wherein the compound is 5-tert-butyl-thiophene-2-sulphonic acid 6-(2-amino-ethoxy)-5-(2-methoxy-phenoxy)-2,2'-bipyrimidin-4-ylamide.

13. The compound of claim 1, wherein $R^1$ is selected from the group consisting of pyridyl; pyridyl substituted with a group selected from the group consisting of $C_{1-7}$-alkyl, halogen, amino, mono-$C_{1-7}$-alkylamino, di-$C_{1-7}$-alkylamino and $C_{1-7}$-alkanoyl; pyrimidinyl; pyrimidinyl substituted with a group selected from the group consisting of $C_{1-7}$-alkyl, halogen, amino, mono-$C_{1-7}$-alkylamino, di-$C_{1-7}$-alkylamino and $C_{1-7}$-alkanoyl; isoxazolyl; isoxazolyl substituted with a group selected from the group consisting of $C_{1-7}$-alkyl, halogen, amino, mono-$C_{1-7}$-alkylamino, di-$C_{1-7}$-alkylamino and $C_{1-7}$-alkanoyl; furyl; furyl substituted with a group selected from the group consisting of $C_{1-7}$-alkyl, halogen, amino, mono-$C_{1-7}$-alkylamino, di-$C_{1-7}$-alkylamino and $C_{1-7}$-alkanoyl; thienyl; and thienyl substituted with a group selected from the group consisting of $C_{1-7}$-alkyl, halogen, amino, mono-$C_{1-7}$-alkylamino, di-$C_{1-7}$-alkylamino and $C_{1-7}$-alkanoyl.

14. The compound according to claim 4 selected from the group consisting of:

pyridin-2-ylcarbamic acid 2-[6-(5-tert-butyl-thiophen-2-ylsulphonylamino)-5-(2-methoxy-phenoxy)-2,2'-bipyrimidin-4-yloxy]-ethyl ester, pyridin-2-ylcarbamic acid 2-[5-(2-methoxy-phenoxy)-6-(5-pentyl-thiophen-2-ylsulphonylamino)-2,2'-bipyrimidin-4-yloxy]-ethyl ester, pyridin-2-ylcarbamic acid 2-[6-[5-(2,2-dimethylpropionyl)-thiophen-2-ylsulphonylamino]-5-(2-methoxy-phenoxy)-2, 2'-bipyrimidin-4-yloxy]-ethyl ester, pyridin-2-ylcarbamic acid 2-[6-(5-isopropyl-pyridin-2-ylsulphonylamino)-5-(2-methoxy-phenoxy)-2,2'-bipyrimidin-4-yloxy ]-ethyl ester, pyridin-2-ylcarbamic acid 2-[5-(2-methoxy-phenoxy)-6-pyridin-2-ylsulphonylamino)-2,2'-bipyrimidin-4-yloxy]-ethyl ester, pyridin-2-ylcarbamic acid 2-[5-(2-methoxy-phenoxy)-6-pyridin-3-ylsulphonylamino)-2,2'-bipyrimidin-4-yloxy]-ethyl ester, pyridin-2-ylcarbamic acid 2-[6-(5-tert-butyl-thiophen-2-ylsulphonylamino)- 5-(2-chloro-5-methoxy-phenoxy)-pyrimidin-4-yloxy ]-ethyl ester, pyridin-4-ylcarbamic acid 2-[6-(5-tert-butyl-thiophen-2-ylsulphonylamino)-5-(2-chloro-5-methoxy-phenoxy)-pyrimidin-4-yloxy]-ethyl ester, pyridin-2-yl-carbamic acid 2-[6-(5-isopropyl-pyridin-2-ylsulphonylamino)-5-(2-methoxy-phenoxy)-2-(3-methoxy-phenyl)-pyrimidin-4-yloxy]-ethyl ester, pyridin-2-ylcarbamic acid 2-[6-(5-isopropyl-pyridin-2-ylsulphonylamino)-5-(2-methoxy-phenoxy)-2-methylsulphanyl-pyrimidin-4-yloxy]-ethyl ester, pyridin-2-ylcarbamic acid 2-[2-(1,3-benzodioxol-5-yl)-6-(5-isopropyl-pyridin-2-ylsulphonylamino)-5-(2-methoxy-phenoxy)-pyrimidin-4-yloxy]-ethyl ester, pyridin-2-ylcarbamic acid 2-[5-(2-chloro-5-methoxy-phenoxy)-6-(5-isopropyl-pyridin-2-ylsulphonylamino)-2-morpholin-4-ylpyrimidin-4-yloxy]-ethyl ester, pyridin-2-ylcarbamic acid 2-[5-(2-methoxy-phenoxy)-6-(5-methyl-pyridin-2-ylsulphonylamino)-2,2'-bipyridimin-4-yloxy]-ethyl ester, pyridin-2-yl-carbamic acid 2-[5-(2-methoxy-phenoxy)-6-(5-methyl-pyridin-2-ylsulphonylamino)-2-morpholin-4-yl-pyrimidin-4-yloxy]-ethyl ester, pyridin-2-ylcarbamic acid 2-[5-(2-chloro-5-methoxy-phenoxy)-6-(5-isopropyl-pyridin-2-sulphonylamino)-2-morpholin-4-yl-pyrimidin-4-yl-methoxy]-ethyl ester, pyridin-2-ylcarbamic acid 5-(2-chloro-5-methoxy-phenoxy)-6-(5-isopropyl-pyridin-2 -ylsulphonylamino)-2-morpholin-4-yl-pyrimidin-4-ylmethyl ester, pyridin-2-ylcarbamic acid 2-[6-(5-isopropyl-pyridin-2-ylsulphonylamino)-5-(2-methoxy-phenoxy)-2-morpholin-4-ylpyrimidin-4-yloxy]ethyl ester pyridin-2-ylcarbamic acid 2-[6-(2,5-dichlorothiophen-3-ylsulphonylamino)-5-(2-methoxy-phenoxy)-2,2'-bipyrimidin-4-yloxy]ethyl ester, pyridin-2-ylcarbamic acid 2-[5-(2-methoxy-phenoxy)-6-(3,5-dimethyl-isoxazol-4-ylsulphonylamino)-2,2'-bipyrimidin-4-yloxy]ethyl ester, pyridin-2-ylcarbamic acid 2-[6-(5-tert-Butylthiophen-2-ylsulphonylamino)-5-( 2-methoxy-phenoxy)-2-morpholin-4-yl-pyrimidin-4-yloxy]-ethyl ester, pyridin-2-ylcarbamic acid 2-[6-(2,5-dichloro-thiophen-3-ylsulphonylamino)-5-(2-methoxy-phenoxy)-2-morpholin-4-yl-pyrimidin-4-yloxy]-ethyl ester, pyridin-2-ylcarbamic acid 2-[6-(3,5-dimethyl-isoxazol-4-ylsulphonylamino)-5-(2-methoxy-phenoxy)-2-morpholin-4-yl-pyrimidin-4-yloxy]-ethyl ester.

15. The compound of claim 5, wherein the compound is carboxylic acid furan-3-ylmethyl ester 2-[5-(2-methoxy-phenoxy)-6-(5-methyl-pyridin-2-sulphonylamino)-2-morpholin-4-yl-pyrimidin-4-yloxy]-ethyl ester.

16. The compound of claim 6, wherein the compound is 5-tert-butyl-thiophene-2-sulphonic acid 5-(2-methoxy-phenoxy)-6-[2-(3-pyridin-2-yl-ureido)-ethoxy]-2,2'-bipyrimidin-4-ylamide, or
5-isopropyl-pyridine-2-sulphonic acid 5-(2-methoxy-phenoxy)-6-[2-(3-pyridin-2-yl-ureido)-ethoxy]-2,2'-bipyrimidin-4-ylamide.

17. A compound of the formula:

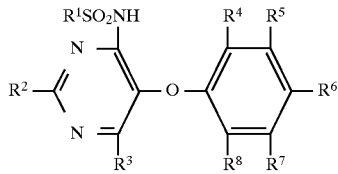

wherein
$R^1$ is selected from the group consisting of pyridyl; pyridyl substituted with a group selected from the group consisting of lower-alkyl, halogen, amino, mono-lower-alkylamino, di-lower-alkylamino and lower-alkanoyl; pyrimidinyl; pyrimidinyl substituted with a group selected from the group consisting of lower-alkyl, halogen, amino, mono-lower-alkylamino, di-lower-alkylamino and lower-alkanoyl; furyl; furyl substituted with a group selected from the group consisting of lower-alkyl, halogen, amino, mono-lower-alkylamino, di-lower-alkylamino and lower-alkanoyl; thienyl; and thienyl substituted with a group selected from the group consisting of lower-alkyl, halogen, amino, mono-lower-alkylamino, di-lower-alkylamino, and lower alkanoyl;

$R^2$ is selected from the group consisting of hydrogen; lower-alkyl; lower-alkoxy; lower-alkylthio; lower-alkoxy-lower-alkyl; lower-alkylsulphonyl-lower-alkoxy; phenyl; lower alkylphenyl; lower-alkoxy-phenyl; lower-alkylenedioxyphenyl; phenyl-lower alkyl; lower alkyl-phenyl-lower alkyl; lower alkoxy-phenyl-lower alkyl; lower alkylenedioxyphenyl-lower alkyl; pyrimidinyl; pyridyl; morpholino; thiomorpholino; piperidino; pyrrolidino; and benzodioxolyl;

$R^3$ is selected from the group consisting of lower-alkyl, lower-alkoxy, formyl, halo-lower-alkyl, hydroxy-lower-alkyl, amino-lower-alkyl, —CH$_2$O—A—lower-alkyl, —(CH$_2$)$_m$—O—(CR$^a$R$^b$)$_n$OH, —(CH$_2$)$_m$—O—(CR$^a$R$^b$)—$_n$ OR$^9$, —(CH$_2$)$_m$—O—(CR$^a$R$^b$)$_n$—Y—R$^9$;

$R^4$–$R^8$ each are selected from the group consisting of hydrogen, lower-alkoxy, or halogen;

$R^9$ is selected from the group consisting of pyridyl; pyrimidinyl; furyl; phenyl; and phenyl substituted with a group selected from the group consisting of lower-alkyl, lower-alkoxy, and halogen;

$R^a$ and $R^b$ each are hydrogen or lower-alkyl;

A is a ketalized 1,2-dihydroxy-ethylene group;

Y is selected from the group consisting of —OC(O)O—, —O(C(O)NH—, —NH(C(O)NH—, and —NHC(O)O—:

n is 2, 3, or 4; and
m is 0 or 1.

18. The compound of claim 17, wherein $R^2$ is selected from the group consisting of hydrogen, pyrimidinyl, pyridyl, morpholino, thiomorpholino, piperidino, pyrrolidino, benzodioxolyl, lower-alkoxyphenyl, and lower-alkylthio.

19. The compound of claim 17, wherein $R^3$ is a residue selected from the group consisting of —O—(CR$^a$R$^b$)$_n$OH, —O—(CR$^a$R$^b$)$_n$NH$_2$, and —O(CH$_2$)$_2$—Y—R$^9$, and R$^9$ is selected from the group consisting of pyridyl, pyrimidinyl, and furyl.

20. The compound of claim 19, wherein $R^3$ is —O(CH$_2$)$_2$—Y—R$^9$ and Y is —(O)C(O)O—.

21. The compound of claim 20, wherein the compound is 5-isopropyl-pyridine-2-sulphonic acid [5-(2-methoxy-phenoxy)-2-mor-pholin-4-yl-6-[2-(pyrimidin-2-yloxy)-ethoxy]-pyrimidin-4-yl]-amide.

22. The compound of claim 17, wherein $R^3$ is hydroxy-ethoxy.

23. The compound of claim 22, wherein the compound is selected from the group consisting of
5-isopropyl-pyridine-sulphonic acid [6-(2-hydroxy-ethoxy)-2-(3-methoxy-benzyl)-5-(2-methoxy-phenoxy)-pyrimidin-4-yl]-amide,
5-isopropyl-pyridine-2-sulphonic acid [6-(2-hydroxy-ethoxy)-2-(3-methoxy-benzyl)-5-phenoxy-pyrmidin-4-yl]-amide,
5-isopropyl-pyridine-2-sulphonic acid [2-(3-hydroxy-benzyl)-6-(2-hydroxy-ethoxy)-5-phenoxy-pyrimidin-4-yl]-amide.

24. The compound of claim 22 which is 5-isopropyl-pyridine-2-sulphonic acid [6-(2-hydroxy-ethoxy)-2-(3-methoxy-benzyl)-5-(2-methoxy-phenoxy)-pyrimidin-4-yl]-amide.

25. The compound of claim 22 which is 5-isopropyl-pyridine-2-sulphonic acid [6-(2-hydroxy-ethoxy)-2-(3-methoxy-benzyl)-5-phenoxy-pyrimidin-4-yl]-amide.

26. The compound of claim 22 which is 5-isopropyl-pyridine-2-sulphonic acid [2-(3-hydroxy-benzyl)-6-(2-hydroxy-ethoxy)-5-phenoxy-pyrimidin-4-yl]-amide.

27. The compound of claim 17, wherein $R^2$ is selected from the group consisting of lower alklphenyl; phenyl-lower alkyl; lower alkyl-phenyl-lower alkyl; lower alkoxy-phenyl-lower alkyl; lower alkylenedioxyphenyl-lower alkyl; pyrimidinyl; pyridyl; morpholino; thiomorpholino; piperidino; pyrrolidino; and benzodioxolyl.

28. A pharmaceutical composition which comprises:
(1) from 3 milligrams to 100 milligrams of a compound of the formula

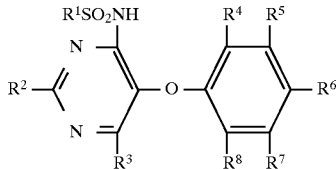

wherein
$R^1$ is a heterocyclyl selected from the group consisting of unsubstituted 2- furyl, 3- furyl, pyrimidinyl, 2-pyridyl, 3-pyridyl, 4-pyridyl, 1,2-diazinyl, 1,4-diazinyl, morpholino, 2-thienyl, 3-thienyl, isoxazolyl, oxazolyl, thiazolyl, imidazolyl, pyrrolyl, benzofuranyl, benzothienyl, indolyl, purinyl, thiomorpholino, piperidino, quinolyl, isoquinolyl and quinazolyl; or heterocyclyl mentioned above mono- or disubstituted with $C_{1-7}$-alkyl, $C_{1-7}$-alkanoyl, halogen, amino, mono-$C_{1-7}$-alkylamino, or di-$C_{1-7}$-alkylamino;

$R^2$ is selected from the group consisting of hydrogen, $C_{1-7}$-alkyl, $C_{1-7}$-alkoxy, $C_{1-7}$-alkylthio, $C_{1-7}$-alkoxy-$C_{1-7}$-alkyl, $C_{1-7}$-alkylsulphonyl-$C_{1-7}$-alkoxy, phenyl, $C_{1-7}$-alkoxy-phenyl, $C_{1-7}$-alkylenedioxyphenyl, and a heterocyclyl selected from the group consisting of unsubstituted 2-furyl, 3-furyl pyrimidinyl, 2-pyridyl, 3-pyridyl, 4-pyridyl, 1,2-diazinyl, 1,4-diazinyl, morpholinoxazolyl, thiazolyl 3-thienyl, isoxazolyl, oxazolyl, thiazolyl, imidazolyl, pyrrolyl, benzofuranyl, benzothienyl, indolyl, purinyl, thiomorpholino, piperidino, quinolyl, isoquinolyl and quinazolyl; or heterocyclyl mentioned above mono- or disubstituted with $C_{1-7}$-alkyl, $C_{1-7}$-alkanoyl, halogen, amino, mono- $C_{1-7}$-alkylamino, or di-$C_{1-7}$-alkylamino;

$R^3$ is selected from the group consisting of $C_{1-7}$-alkyl, $C_{1-7}$-alkoxy, formyl, halo-$C_{1-7}$-alkyl, hydroxy-$C_{1-7}$-alkyl, amino-$C_{1-7}$-alkyl, $-CH_2O-A-C_{1-7}$-alkyl, $-(CH_2)_m-O-(CR^aR^b)_n OH$, $-(CH_2)_m-O-(CR^aR^b)_n NH_2$ and $-(CH_2)_m-O-(CR^aR^b)_n-Y-R^9$;

$R^4-R^8$ each are selected from the group consisting of hydrogen, $C_{1-7}$-alkoxy and halogen;

$R^9$ is a heterocyclyl selected from the group consisting of unsubstituted 2-furyl, 3-furyl, pyrimiminyl, 2-pyridyl, 3-pyridyl, 4- pyridyl, 1,2-diazinyl, 1,4-diazinyl, morpholino, 2-thienyl, 3- thienyl, isoxazolyl, oxazolyl, thiazolyl, imidazolyl, pyrrolyl, benzofuranyl, benzothienyl, indolyl, purinyl, thiomorpholino, piperidino, quinolyl, isoquinolyl and quinazolyl; or heterocyclyl mentioned above mono- or disubstituted with $C_{1-7}$-alkyl, $C_{1-7}$-alkanoyl, halogen, amino, mono- $C_{1-7}$-alkyl amino, or di-$C_{1-7}$-alkylamino; phenyl; and phenyl substituted with the group selected from the group consisting of $C_{1-7}$-alkyl, $C_{1-7}$-alkoxy, halogen and $C_{1-7}$-alkyl;

$R^a$ and $R^b$ each are hydrogen or $C_{1-7}$-alkyl;

A is a ketalized 1,2-dihydroxy-ethylene group;

Y is selected from the group consisting of $-OC(O)O-$, $-O(C(O)NH-$, $-NH(C(O)NH-$ and $-NHC(O)O-$;

n is 2, 3 or 4;

m is 0 or 1; and (2) an inert carrier.

29. The pharmaceutical composition of claim 28 further comprising inert additives, binders, fillers, diluents, preservatives, stabilizers, emulsifiers and flavorants.

30. A pharmaceutical composition which comprises:

(1) from 3 milligrams to 100 milligrams of a compound of the formula

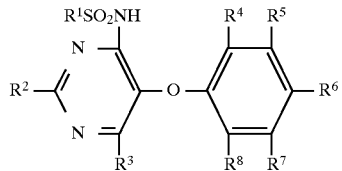

I wherein $R^1$ is selected from the group consisting of pyridyl; pyridyl substituted with a group selected from the group consisting of lower-alkyl, halogen, amino, mono-lower-alkylamino, di-lower-alkylamino and lower-alkanoyl; pyrimidinyl; pyrimidinyl substituted with a group selected from the group consisting of lower-alkyl, halogen, amino, mono-lower-alkylamino, di-lower-alkylamino and lower-alkanoyl; furyl; furyl substituted with a group selected from the group consisting of lower-alkyl, halogen, amino, mono-lower-alkylamino, di-lower-alkylamino and lower-alkanoyl; thienyl; and thienyl substituted with a group selected from the group consisting of lower-alkyl, halogen, amino, mono-lower-alkylamino, di-lower-alkylamino, and lower alkanoyl;

$R^2$ is selected from the group consisting of hydrogen, lower-alkyl; lower-alkoxy; lower-alkylthio; lower-alkoxy-lower-alkyl; lower-alkylsulphonyl-lower-alkoxy; phenyl; lower alkylphenyl; lower-alkoxy-phenyl; lower-alkylenedioxyphenyl; phenyl-lower alkyl; lower alkyl-phenyl-lower alkyl; lower alkoxy-phenyl-lower alkyl; lower alkylenedioxyphenyl-lower alkyl; pyrimidinyl; pyridyl; morpholino; thiomorpholino; piperidino; pyrrolidino; and benzodioxolyl;

$R^3$ is selected from the group consisting of lower-alkyl, lower-alkoxy, formyl, halo-lower-alkyl, hydroxy-lower-alkyl, amino-lower-alkyl, $-CH_2-A-$lower-alkyl, $-(CH_2)_m-O-(CR^aR^b)_n OH$, $-(CH_2)_m-O-(CR^aR^b)_n OR^9$, $(CH_2)_m-O-(CR^aR^b)_n NH_2$ and $-(CH_2)_m-O-(CR^aR^b)n-Y-R^9$;

$R^4-R^8$ each are selected from the group consisting of hydrogen, lower-alkoxy, and halogen;

$R^9$ is selected from the group consisting of pyridyl; pyrimidinyl; furyl; phenyl; and phenyl substituted with a group selected from the group consisting of lower-alkyl, lower-alkoxy, and halogen;

$R^a$ and $R^b$ each are hydrogen or lower-alkyl;

A is a ketalized 1,2-dihydroxy-ethylene group;

Y is selected from the group consisting of $-OC(O)O-$, $-O(C(O)NH-$, $-NH(C(O)NH-$, and $-NHC(O)O-$:

n is 2, 3, or 4; and m is 0 or 1; and (2) an inert carrier.

31. The composition of claim 30, wherein the composition comprises from 10 milligrams to 100 milligrams of the compound of formula 1.

32. The composition of claim 31, wherein the composition comprises 25 milligrams of the compound of formula 1.

33. The composition of claim 30, wherein the composition comprises 3 milligrams of the compound of formula 1.

34. The pharmaceutical composition of claim 30 further comprising inert additives, binders, fillers, diluents, preservatives, stabilizers, emulsifiers, and flavorants.

35. A method for the treatment of disorders associated with vasoconstriction selected from the group consisting of hypertension, ischaemia, vasospasms and angina pectoris comprising administering to a patient having such disorder an effective amount of a compound of formula:

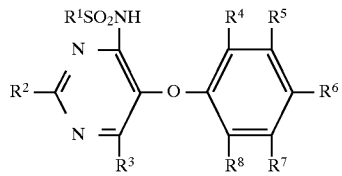

I wherein $R^1$ is a heterocyclyl selected from the group consisting of unsubstituted 2-furyl, 3-furyl, pyrimidinyl, 2-pyridyl, 3-pyridyl, 4-pyridyl, 1,2- diazinyl, 1,4-diazinyl, morpholino, 2-thienyl, 3-thienyl, isoxazolyl, oxazolyl, thiazolyl, imidazolyl, pyrrolyl, benzofuranyl, benzothienyl, indolyl, purinyl, thiomorpholino, piperidino, quinolyl, isoquinolyl and quinazolyl; or heterocyclyl mentioned above mono- or disubstituted with $C_{1-7}$-alkyl, $C_{1-7}$-alkanoyl, halogen, amino, mono- $C_{1-7}$-alkylamino, or di-$C_{1-7}$-alkylamino;

$R^2$ is selected from the group consisting of hydrogen, $C_{1-7}$-alkyl, $C_{1-7}$-alkoxy, $C_{1-7}$-alkylthio, $C_{1-7}$-alkoxy-$C_{1-7}$-alkyl, $C_{1-7}$-alkylsulphonyl-$C_{1-7}$-alkoxy, phenyl, $C_{1-7}$-alkoxy-phenyl, C 7-alkylenedioxyphenyl, and heterocyclyl selected from the group consisting of unsubstituted 2-furyl, 3-furyl, pyrimidinyl, 2-pyridyl, 3-pyridyl, 4-pyridyl, 1,2-diazinyl, 1,4-diazinyl, morpholino, 2-thienyl, 3-thienyl, isoxazolyl, oxazolyl, thiazolyl, imidazolyl, pyrrolyl, benzofuranyl, benzothienyl, indolyl, purinyl, thiomorpholino, piperidino, quinolyl, isoquinolyl and quinazolyl; or heterocyclyl mentioned above mono- or disubstituted with $C_{1-7}$-alkyl, $C_{1-7}$-alkanoyl, halogen, amino, mono- $C_{1-7}$-alkylamino, or di-$C_{1-7}$-alkylamino;

$R^3$ is selected from the group consisting of $C_{1-7}$-alkyl, $C_{1-7}$-alkoxy, formyl, halo-$C_{1-7}$-alkyl, hydroxy-$C_{1-7}$-alkyl, amino-$C_{1-7}$-alkyl, —$CH_2O$—A—$C_{1-7}$-alkyl, —$(CH_2)_m$—O—$(CR^aR^b)_n$OH, —$(CH_2)_m$—O—$(CR^aR^b)_n$NH$_2$ and —$(CH_2)_m$—O—$(CR^aR^b)_n$—Y—$R^9$;

$R^4$–$R^8$ each are selected from the group consisting of hydrogen, $C_{1-7}$-alkoxy and halogen;

$R^9$ is selected from the group consisting of a heterocyclyl selected from the group consisting of unsubstituted 2-furyl, 3-furyl, pyrimidinyl, 2-pyridyl, 3-pyridyl, 4-pyridyl, 1, 2-diazinyl, 1,4-diazinyl, morpholino, 2-thienyl, 3-thienyl, isoxazolyl, oxazolyl, thiazolyl, imidazolyl, pyrrolyl, benzofuranyl, benzothienyl, indolyl, purinyl, thiomorpholino, piperidino, quinolyl, isoquinolyl and quinazolyl; or heterocyclyl mentioned above mono- or disubstituted with $C_{1-7}$-alkyl, $C_{1-7}$-alkanoyl, halogen, amino, mono- $C_{1-7}$-alkylamino, or di-$C_{1-7}$-alkylamino; phenyl; and phenyl substituted with the group selected from the group consisting of $C_{1-7}$-alkyl, $C_{1-7}$-alkoxy, halogen and $C_{1-7}$-alkyl;

$R^a$ and $R^b$ each are hydrogen or $C_{1-7}$-alkyl;

A is a ketalized 1,2-dihydroxy-ethylene group;

Y is selected from the group consisting of —OC(O)O—, —O(C(O)NH—, —NH(C(O)NH—and —NHC(O)O—;

n is 2, 3 or 4; and m is 0 or 1.

36. The method of claim 35, wherein the effective amount is from about 0.1 to about 100 mg/kg body weight per day.

37. A method for the treatment of disorders associated with vasoconstriction selected from the group consisting of hypertension, ischaemia, vasospasms and angina pectoris comprising administering to a patient having such disorder an effective amount of a compound of formula:

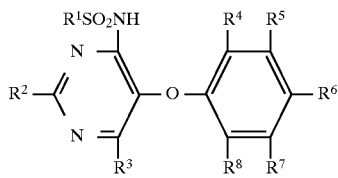

I $R^1$ is selected from the group consisting of pyridyl; pyridyl substituted with a group selected from the group consisting of lower-alkyl, halogen, amino, mono-lower-alkylamino, di-lower-alkylamino and lower-alkanoyl; pyrimidinyl; pyrimidinyl substituted with a group selected from the group consisting of lower-alkyl, halogen, amino, mono-lower-alkylamino, di-lower-alkylamino and lower-alkanoyl; furyl; furyl substituted with a group selected from the group consisting of lower-alkyl, halogen, amino, mono-lower-alkylamino, di-lower-alkylamino and lower- alkanoyl; thienyl; and thienyl substituted with a group selected from the group consisting of lower-alkyl, halogen, amino, mono-lower-alkylamino, di-lower-alkylamino, and lower alkanoyl;

$R^2$ is selected from the group consisting of hydrogen; lower-alkyl;

lower-alkoxy; lower-alkylthio; lower-alkoxy-lower-alkyl; lower-alkylsulphonyl-lower-alkoxy; phenyl; lower alkylphenyl; lower-alkoxy-phenyl; lower-alkylenedioxyphenyl; phenyl-lower alkyl; lower alkyl-phenyl-lower alkyl; lower alkoxy-phenyl-lower alkyl; lower alkylenedioxyphenyl-lower alkyl; pyrimidinyl; pyridyl; morplolino; thio morpholino; piperidino; pyrrolidino; and benzodioxolyl; alkyl;

$R^3$ is selected from the group consisting of lower-alkyl, lower-alkoxy, formyl, halo-lower-alkyl, hydroxy-lower-alkyl, amino-lower-alkyl, —$CH_2O$—A—lower-alkyl, —$(CH_2)_m$—O—$(CR^aR^b)_n$OH, $(CH_2)_m$—O—$(CR^aR^b)$—$_nOR^9$, —$(CH2)_m$—O—$(CR^aR^b)$ $_nNH_2$, and —$(CH_2)_m$O—$(CR^aR^b)_n$—Y—$R^9$;

$R^4$–$R^8$ each are selected from the group consisting of hydrogen, lower-alkoxy, and halogen;

$R^9$ is selected from the group consisting of pyridyl; pyrimidinyl; furyl; phenyl; and phenyl substituted with a group selected from the group consisting of lower-alkyl, lower-alkoxy, and halogen;

$R^a$ and $R^b$ each are hydrogen or lower-alkyl;

A is a ketalized 1, 2-dihydroxy-ethylene group;

Y is selected from the group consisting of —OC(O)O—, —O(C(O)NH—, —NH(C(O)NH—, and —NHC(O)O—:

n is 2, 3, or 4; and m is O or 1.

38. The method of claim 37, wherein the effective amount is from about 0.1 to about 100 mg/kg body weight per day.

39. The compound of claim 7, wherein the compound is selected from the group consisting of 5-lsopropyl-pyridine-2-sulphonic acid 5-(2-chloro-5-methoxy-phenoxy)-6-methyl-2-morpholin-4-yl-pyrimidin-4-ylamide, 5-(2-chloro-5-methoxy-phenoxy)-6-formyl-2-morpholin-4-yl-pyrimidin-4-ylamide, 5-isopropyl-pyridine-2-sulphonic acid 5-(2-chloro-5-methoxy-phenoxy)-6-hydroxymethyl-2-morpholin-4-yl-pyrimidin-4-ylamide, 5-isopropyl-pyridine-2-sulphonic acid 5-(2-chloro-5-methoxy-phenoxy)-6-chloromethyl-2-morpholin-4-yl-pyrimidin-4-ylamide, 5-(2-chloro-5-methoxy-phenoxy)-6-(2-hydroxy-ethoxymethyl)-2-morpholin-4-yl-pyrimidin-4-ylamide.

* * * * *

UNITED STATES PATENT AND TRADEMARK OFFICE
CERTIFICATE OF CORRECTION

PATENT NO. : 5,837,708
DATED : November 17, 1998
INVENTOR(S) : Volker Breu et al.

It is certified that error appears in the above-identified patent and that said Letters Patent is hereby corrected as shown below:

Column 24, claim 1, line 12, "-O-$(CR^a_R{}^b)_n$-" should be -- -O-$(CR^aR^b)_n$- --

Column 24, claim 5, line 49, "-O$(CH^2)_2$-Y-$R^9$ and Y is NHC(O)NH-" should be -- -O$(CH_2)_2$-Y-$R^9$ and Y is NHC(O)NH-. --

Column 27, claim 17, line 50, after "$OR^9$," insert -- -$(CH_2)_m$-O-$(CR^aR^b)_n NH_2$, and --

Column 28, claim 21, line 12, "-2-mor-pholin-" should be -- 2-morpholin- --

Column 29, claim 28, line 5, delete "morpholinoxazolyl, thiazolyl" and insert -- morpholino, 2-thienyl, --

UNITED STATES PATENT AND TRADEMARK OFFICE
CERTIFICATE OF CORRECTION

PATENT NO. : 5,837,708
DATED : November 17, 1998
INVENTOR(S) : Volker Breu et al.

It is certified that error appears in the above-identified patent and that said Letters Patent is hereby corrected as shown below:

Column 30, claim 30, line 17, "-$CH_2$-A-lower-" should be -- -$CH_2$O-A-lower- --

Column 31, claim 35, line 7, "C 7-alkylenedioxyphenyl," should be -- $C_{1-7}$-alkylenedioxyphenyl, --.

Signed and Sealed this

First Day of June, 1999

Attest:

Attesting Officer

Q. TODD DICKINSON

Acting Commissioner of Patents and Trademarks